United States Patent
Birukov et al.

(10) Patent No.: US 10,954,255 B2
(45) Date of Patent: Mar. 23, 2021

(54) PHOSPHOLIPID ANALOGUES

(71) Applicants: Karl-Franzens-Universitaet Graz, Graz (AT); University of Chicago, Chicago, IL (US)

(72) Inventors: Konstantin Birukov, Fulton, MD (US); Anna Birukova, Fulton, MD (US); Valery Bochkov, Graz (AT); Olga Oskolkova, Graz (AT)

(73) Assignees: Karl-Franzens-Universitaet Graz, Graz (AT); University of Chicago, Chicago, IL (US)

( * ) Notice: Subject to any disclaimer, the term of this patent is extended or adjusted under 35 U.S.C. 154(b) by 0 days.

(21) Appl. No.: 16/635,883

(22) PCT Filed: Jul. 27, 2018

(86) PCT No.: PCT/EP2018/070481
§ 371 (c)(1),
(2) Date: Jan. 31, 2020

(87) PCT Pub. No.: WO2019/025324
PCT Pub. Date: Feb. 7, 2019

(65) Prior Publication Data
US 2020/0157127 A1    May 21, 2020

(51) Int. Cl.
C07F 9/117 (2006.01)
C07F 9/10 (2006.01)

(52) U.S. Cl.
CPC ............. *C07F 9/117* (2013.01); *C07F 9/10* (2013.01)

(58) Field of Classification Search
CPC .................................. C07F 9/117; C07F 9/10
See application file for complete search history.

(56) References Cited

U.S. PATENT DOCUMENTS 5,158,942 A    10/1992 Herrmann et al.

FOREIGN PATENT DOCUMENTS

DE    26 42 661 A1    3/1978
EP    0 416 401 A2    3/1991
(Continued)

OTHER PUBLICATIONS

International Search Report for PCT/EP18/070481 dated Oct. 5, 2018 (5 pages).
(Continued)

Primary Examiner — Alicia L Otton

(74) *Attorney, Agent, or Firm* — Thrive IP®; Jeremy M. Stipkala; William La Salle, III

(57) ABSTRACT

The present invention relates to a compound having a structure according to formula (I) or a salt thereof, wherein: $R_1$ is a branched or linear alkyl, acyl, alkenyl, hydroxyalkyl, hydroxyalkenyl, or hydroxy-alkinyl residue comprising 6 to 30 carbon atoms, $R_2$ is selected from the group consisting of: a) an alkyl residue comprising 1 to 10 carbon atoms and comprising a terminal or cyclic quaternary ammonium, b) an alkyl residue comprising 1 to 10 carbon atoms and comprising a terminal amino group and/or 1 to 3 hydroxyl groups, c) an amino acid residue, d) a five or six carbon sugar and e) H, $R_3$ is a residue selected from the group consisting of an alkyl, alkenyl, prostanyl-dialkyl, furanyl-dialkyl, cyclobutyl-dialkyl, cycloalkyl and aryl group of 2 to 40 carbon atoms length and comprising at least one keto group, epoxy group, aldehyde group, peroxy group, hydroperoxy group, hydroxyl group or a free carboxyl group, L1 is selected from the group consisting of O, NH, S, $CH_2$, (aa), (bb), (cc), (dd), (ee), (ff), (gg), (hh), (ii), (jj), (kk), (ll), (mm), or (nn), L2 is an amide group or an ether group, X and Z are independently O, S or $CH_2$, and Y is selected from the group consisting of O and S.

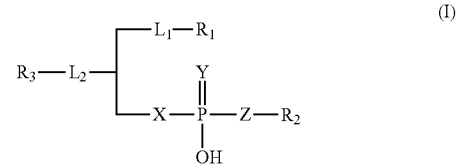

(I)

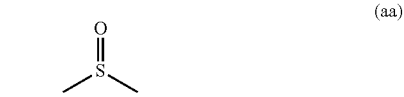

(aa)

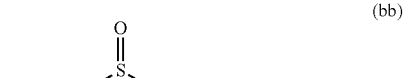

(bb)

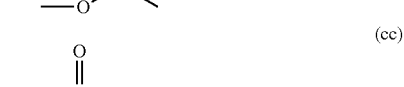

(cc)

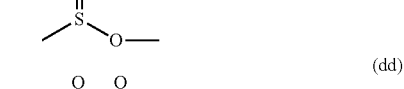

(dd)

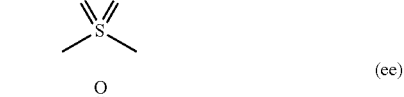

(ee)

(ff)

(gg)

(Continued)

-continued

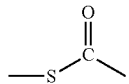 (hh)

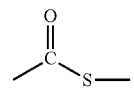

(ii)

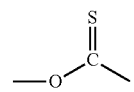

(jj)

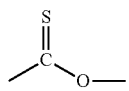

(kk)

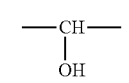

(ll)

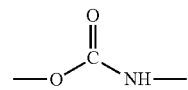

(mm)

-continued

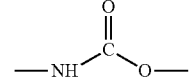 (nn)

20 Claims, 13 Drawing Sheets

(56) References Cited

FOREIGN PATENT DOCUMENTS

| WO | 95/00649 A1 | 1/1995 |
| WO | 96/40694 A1 | 12/1996 |
| WO | 2005/039504 A2 | 5/2005 |

OTHER PUBLICATIONS

International Preliminary Report on Patentability for PCT/EP18/070481 dated Jul. 15, 2019 (6 pages).
Bartel, M. et al., "Synthesis of enantiomerically pure, sn-1 modified sn-2-deoxy-2-amido-glycero-3-phospholipids," Chemistry and Physics of Lipids, vol. 107, No. 1, pp. 121-129 (Sep. 1, 2000).
Pedersen, P.J. et al., "Prostaglandin phospholipid conjugates with unusual biophysical and cytotoxic properties," Bioorg. & Med. Chem. Lett., vol. 20, No. 15, pp. 4456-4458 (Jun. 2010).
Deigner, H., "Novel reversible, irreversible and fluorescent inhibitors of patelet-activating factor acetylhydrolase as mechanistic probes," Atherosclerosis vol. 144, No. 1, pp. 79-90 (May 1, 1999).
Tan, D. et al., "Double-chain phospholipid end-capped polyurethanes: Synthesis, characterization and platelet adhesion study," Applied Surface Sci., vol. 258, No. 7, pp. 2687-2706 (Oct. 23, 2011).

PHOSPHOLIPID ANALOGUES

STATEMENT REGARDING FEDERALLY-SPONSORED RESEARCH OR DEVELOPMENT

This invention was made with U.S. government support under grants HL076259, HL087823, and HL107920 awarded by the National Institutes of Health. The U.S. government has certain rights in the invention.

CROSS-REFERENCE TO RELATED APPLICATIONS

This application represents the U.S. National Phase under 35 U.S.C. § 371 of International Patent Application No. PCT/EP2018/070481, filed internationally on 27 Jul. 2018, and entitled, "Phospholipid Analogues," which claims the priority of U.S. Non-Provisional patent application Ser. No. 15/667,893, filed 3 Aug. 2017. The foregoing international patent application and U.S. non-provisional patent application are both incorporated herein by reference in their entirety.

TECHNICAL FIELD

The present invention relates to the field of compounds, in particular to phospholipid analogues, which can be used to treat conditions like sepsis and conditions associated with inflammation.

BACKGROUND ART

Severe sepsis is a leading cause of death in the United States and Austria and the most common cause of death among critically ill patients in non-coronary intensive care units (ICU). Respiratory tract infections, particularly pneumonia, are the most common site of infection, and associated with the highest mortality. The type of organism causing severe sepsis is an important determinant of outcome, and gram-positive organisms as a cause of sepsis have increased in frequency over time and are now more common than gram-negative infections. In the United States, the incidence of severe sepsis is estimated to be 300 cases per 100000 population (>0.5 million cases per year, with at least a third being lethal). In Austria the incidence of sepsis is between 50 to 95 cases per 100000 population, thus about 18000 cases of sepsis per year, with half of them being severe forms. With 7500 deaths per year, sepsis is the third most frequent cause of lethality in Austria.

The acute respiratory distress syndrome (ARDS), which is characterized by a combination of lung edema and acute inflammation, continues to be a major health care problem, affecting more than 190,000 people in the US annually with a mortality of 27-45% depending on the severity of the illness and co-morbidities. Estimates from prospective US cohort studies range from 64.2 to 78.9 cases per 100000 persons per year, whereas estimates from other countries have shown lower but still significant rates: Northern Europe—17 cases/100000 and Australia/New Zealand—34 cases/100000 population.

In summary, sepsis and ARDS are frequent and extremely severe conditions very often leading to the death of patients. The high mortality in sepsis and ARDS points to the low efficiency of existing treatment modalities and justifies the need for development of novel methods and drugs for therapy.

Current options for treatment of sepsis and ARDS include:
- Infection treatment (antibiotics) and infection prevention (Selective oral decontamination and selective digestive decontamination)
- Hemodynamic control (fluid therapy, vasopressors) and adjunctive therapy
- Inotropic therapy and corticosteroids
- Administration of blood products
- Mechanical ventilation in sepsis-induced ARDS
- Prophylaxis of deep vein thrombosis Although these treatments target a variety of pathogenic events, a reliable correction of two important disease mechanisms is still not achieved. Currently there are no clinically effective drugs targeting two key pathogenetic mechanisms such as hyperactivation of innate immune system by bacteria and impairment of lung endothelial barrier responsible for edema formation. Although the efficiency of these therapeutic modalities is well shown in preclinical models, translation into the clinical practice is still pending. The present invention provides a solution for both issues, namely a compound that simultaneously inhibits activation of innate immunity by bacteria and at the same time improves the endothelial barrier.

SUMMARY OF INVENTION

The present invention relates to a compound having a structure according to formula (I)

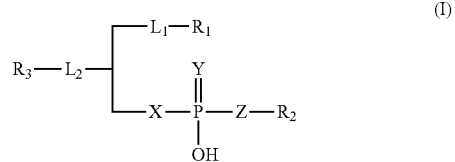

or a salt thereof, wherein $R_1$ is a branched or linear alkyl, acyl, alkenyl, hydroxyalkyl, hydroxyalkenyl, or hydroxy-alkinyl residue comprising 6 to 30 carbon atoms, $R_2$ is selected from the group consisting of
a) an alkyl residue comprising 1 to 10 carbon atoms and comprising a terminal or cyclic quaternary ammonium,
b) an alkyl residue comprising 1 to 10 carbon atoms and comprising a terminal amino group and/or 1 to 3 hydroxyl groups,
c) an amino acid residue,
d) a five or six carbon sugar and
e) H, $R_3$ is a residue selected from the group consisting of an alkyl, alkenyl, prostanyl-dialkyl, furanyl-dialkyl, cyclobutyl-dialkyl, cycloalkyl and aryl group of 2 to 40 carbon atoms length and comprising at least one keto group, epoxy group, aldehyde group, peroxy group, hydroperoxy group, hydroxyl group or a free carboxyl group, L1 is selected from the group consisting of O, NH, S, $CH_2$,

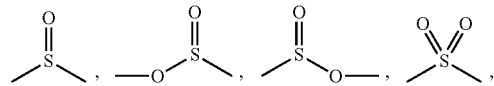

-continued

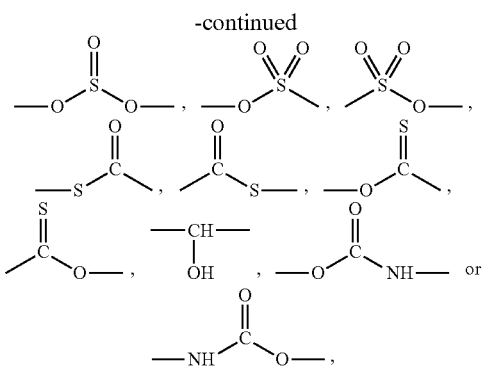

L2 is an amide group or an ether group,
X and Z are independently O, S or $CH_2$, and
Y is selected from the group consisting of O and S.

In an embodiment of the present invention R1 is a residue selected from the group consisting of hexyl group, heptyl group, octyl group, nonyl group, decyl group, undecyl group, dodecyl group, tetradecyl group, hexadecyl group and octadecyl group In a further embodiment of the present invention the R2 is a choline residue.

In an embodiment of the present invention R2 is inositol, glycerol, ethanolamine, H or serine.

In another embodiment of the present invention R3 is selected from a group consisting of prostaglandins, isoprostanes, lipoxins, resolvins, protectins and maresins, monohydroxy-, dihydroxy-, trihydroxy-, tetrahydroxy fatty acid residues with epoxy-, keto-, hydroperoxy-, hydroxyl- or prostane groups independent on regio- and stereo-position of substituents within their structures.

In an embodiment of the present invention the oxylipin is preferably selected from the group consisting of prostacyclins, prostaglandins, preferably products of prostaglandin metabolism (e.g., keto-prostaglandins, deoxyprostaglandins, hydroxy-prostaglandins, dihydro-keto-prostaglandins), isoprostanes (for example, 8-isoprostaglandin E2), lipoxins (for example, lipoxin A4), maresins (e.g., maresin 1), resolvins (e.g., resolving E1) and protectins (e.g., protectin D1).

In another embodiment of the present invention the prostaglandin is selected from the group consisting of prostaglandin E2, prostaglandin E1, prostaglandin A2, prostaglandin F2α, prostaglandin B2, prostaglandin C2, prostaglandin D2, prostaglandin J2, 15-deoxy-Δ12,14-prostaglandin J2, deoxyprostaglandin D2, deoxyprostaglandin E2, deoxyprostaglandin A2,15-keto-prostaglandin F2α, 15-keto-prostaglandin E2, and epoxyprostaglandin E2.

In a further embodiment of the present invention the isoprostane is selected from the group consisting of isoprostaglandin E2, isoprostaglandin A2, isoprostaglandin F2α, isoprostaglandin B2, isoprostaglandin C2, isoprostaglandin D2, isoprostaglandin J2, deoxyisoprostaglandin D2, deoxyisoprostaglandin E2, deoxyisoprostaglandin A2, deoxyisoprostaglandin J2, 15-keto-isoprostaglandin F2α, 15-keto-isoprostaglandin E2, epoxyisoprostaglandin E2.

The above mentioned prostaglandins and isoprostanes are originated from arachidonic acid. Similar oxylipin compounds originated from other polyunsaturated fatty acids containing at least 3 double bonds (e.g., linolenic, eicosatetraenoic acid, eicosatetraenoic acid, eicosapentaenoic acid, docosatrienoic acid, docosahexaenoic acid etc.) can be also used.

Analogs of prostaglandins or isoprostanes containing sulfur or nitrogen can also be used.

In an embodiment of the present invention the lipoxin is selected from the group consisting of lipoxin A4, lipoxin B4 and 15(R)-lipoxin A4.

In another embodiment of the present invention the maresin is selected from the group consisting of maresin 1 and maresin 2.

In an embodiment of the present invention the resolvin is selected from the group consisting of resolvin E1, resolvin T1, resolvin D1 and resolvin D2.

In a further embodiment of the present invention the protectin is selected from the group consisting of protectin PDX and protectin D1.

In a further embodiment of the present invention the prostacyclin or prostacyclin-like compound is selected from the group consisting of 5-{(E)-(1S,5S,6R,7R)-7-hydroxy-6[(E)-(3S,4RS)-3-hydroxy-4-methyl-1-octen-6-inyl]-bicyclo[3.3.0]octan-3-ylidene}pentanoyl (iloprost), 5-cis-iloprost, 5-cis-15(R)-iloprost, 15(R)-iloprost, 15-keto-iloprost, carbaprostacyclin, 5-cis-carbaprostacyclin, 13,14-dehydro-15-cyclohexyl, 5Z-[3aR,3-difluorohexahydro-5R-hydroxy-4R-[3R-hydroxy-4S-methyl-1E-nonen-6aS-ynyl]-2H-cyclopenta[b]furan-2-ylidene]-pentanoyl (16(R)-AFP07), 5Z-[(3aR,4R,5R,6aS)-3,3-difluorohexahydro-5-hydroxy-4-[(1E,3S,4S)-3-hydroxy-4-methyl-1-nonen-6-ynyl]-2H-cyclopenta[b]furan-2-ylidene]-pentanoyl (AFP07), treprostinil, cicaprost, beraprost, ciprostene and 15(R)-prostaglandin $I_2$.

In an embodiment of the present invention R3 is a compound selected from the group consisting of 10-hydroxydecanyl, 12-hydroxydodecanyl, 15-hydroxyeicosatetraenyl, 12-hydroxy eicosatetraenyl, 8-hydroxyeicosatetraenyl, 9-hydroxyeicosatetrenyl, D,L-threo-9,10,16-trixydroxyhexadecanyl (aleuritic acid residue), (R)-12-hydroxy-cis-9-octadecanyl (12-hydroxyoleic acid or ricinoleic acid residue).

In another embodiment of the present invention $L_1$ is O and/or L2 is an amide group.

In a further embodiment of the present invention X, Y and Z are O.

In an embodiment of the present invention the compound is selected from the group consisting of

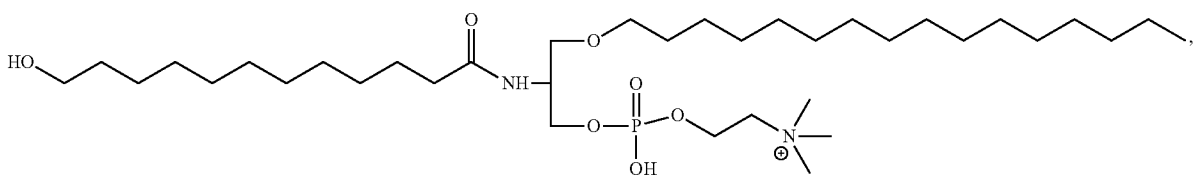

-continued
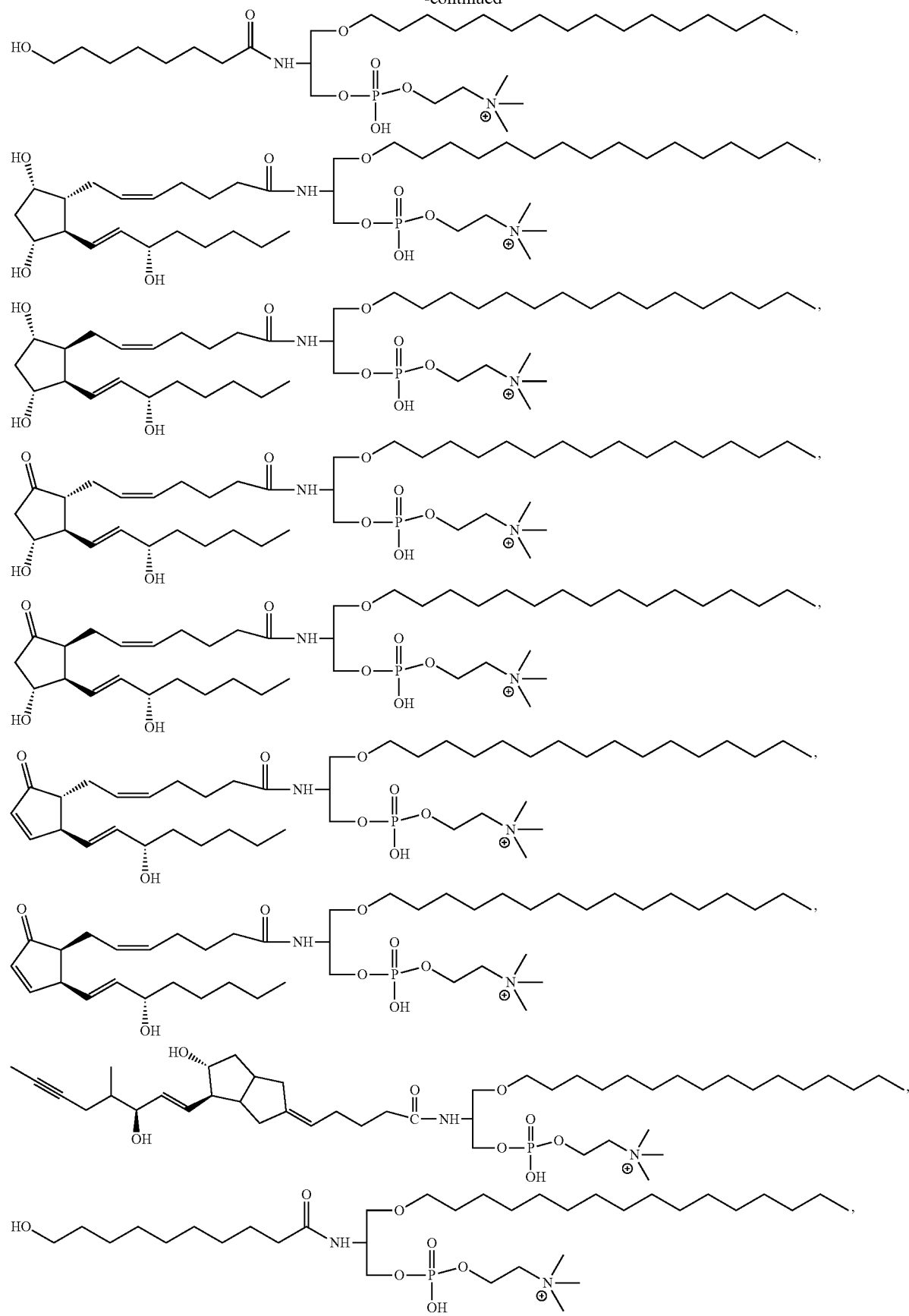

-continued
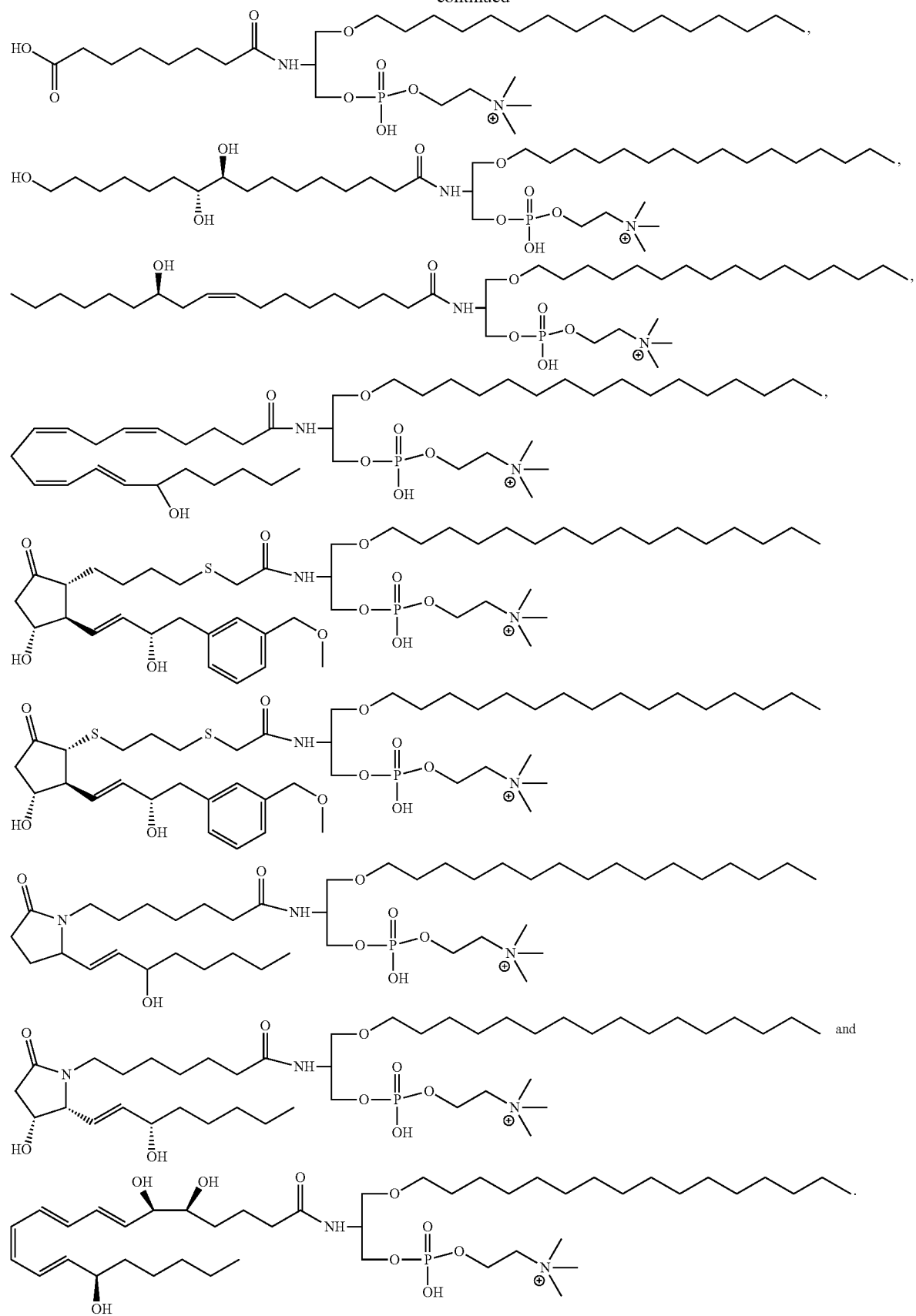

A further aspect of the present invention relates to a pharmaceutical composition comprising a compound according to the present invention.

Another aspect of the present invention relates to a method for treating an inflammatory disease or disorder or a disease or disorder associated with Toll-like receptor 2 (TLR2) and/or Toll-like receptor 4 (TLR4) and/or NFkB inflammatory cascade comprising the administration of a compound or a pharmaceutical composition according to the present invention to a mammal in need thereof.

In an embodiment of the present invention the mammal is a human.

In a further preferred embodiment of the present invention the inflammatory disease or disorder associated with Toll-like receptor 2 (TLR2) and/or Toll-like receptor 4 (TLR4) is sepsis, preferably Gram-negative, Gram-positive or mixed-type sepsis.

In another embodiment of the present invention the inflammatory condition is selected from the group consisting of acute respiratory distress syndrome (ARDS), transfusion associated lung injury (TRALI), ventilator induced lung injury (VILI), high altitude pulmonary edema, exacerbation of lung inflammation associated with pulmonary fibrosis and cystic fibrosis, acute chest syndrome associated with sickle cell disease, lung injury secondary to sepsis, necrotizing pancreatitis, brain injury, multiple organ failure and hemorrhagic shock.

In an embodiment of the present invention the condition associated with TLR2 and/or TLR4 is selected from the group consisting of acute inflammatory states, preferably major trauma or burns, and chronic inflammatory states, preferably systemic inflammatory response syndrome, stroke, ischemia-reperfusion-induced damage of any organ, preferably infarction or transplantation of any organ, acetaminophen-induced liver damage, non-alcoholic steatohepatitis, inflammatory bowel disease, neuroinflammatory diseases, preferably Alzheimer disease, Parkinson disease, amyotrophic lateral sclerosis or epilepsy.

Another aspect of the present invention relates to a compound according to the present invention or a pharmaceutical composition according to the present invention for use in the treatment of an inflammatory condition or a condition associated with Toll-like receptor 2 (TLR2) and/or Toll-like receptor 4 (TLR4) and/or NFkB inflammatory cascade in mammals.

In an embodiment of the present invention the inflammatory disease or disorder associated with Toll-like receptor 2 (TLR2) and/or Toll-like receptor 4 (TLR4) is sepsis, preferably Gram-negative, Gram-positive or mixed-type sepsis.

In an embodiment of the present invention the inflammatory condition is selected from the group consisting of acute respiratory distress syndrome (ARDS), transfusion associated lung injury (TRALI), ventilator induced lung injury (VILI), high altitude pulmonary edema, exacerbation of lung inflammation associated with pulmonary fibrosis and cystic fibrosis, acute chest syndrome associated with sickle cell disease, lung injury secondary to sepsis, necrotizing pancreatitis, brain injury, multiple organ failure and hemorrhagic shock.

In a further embodiment of the present invention the condition associated with TLR2 and/or TLR4 is selected from the group consisting of acute inflammatory states, preferably major trauma or burns, and chronic inflammatory states, preferably systemic inflammatory response syndrome, stroke, ischemia-reperfusion-induced damage of any organ, preferably infarction or transplantation of any organ, acetaminophen-induced liver damage, non-alcoholic steatohepatitis, inflammatory bowel disease, neuroinflammatory diseases, preferably Alzheimer disease, Parkinson disease, amyotrophic lateral sclerosis or epilepsy.

DESCRIPTION OF EMBODIMENTS

Figure 1:
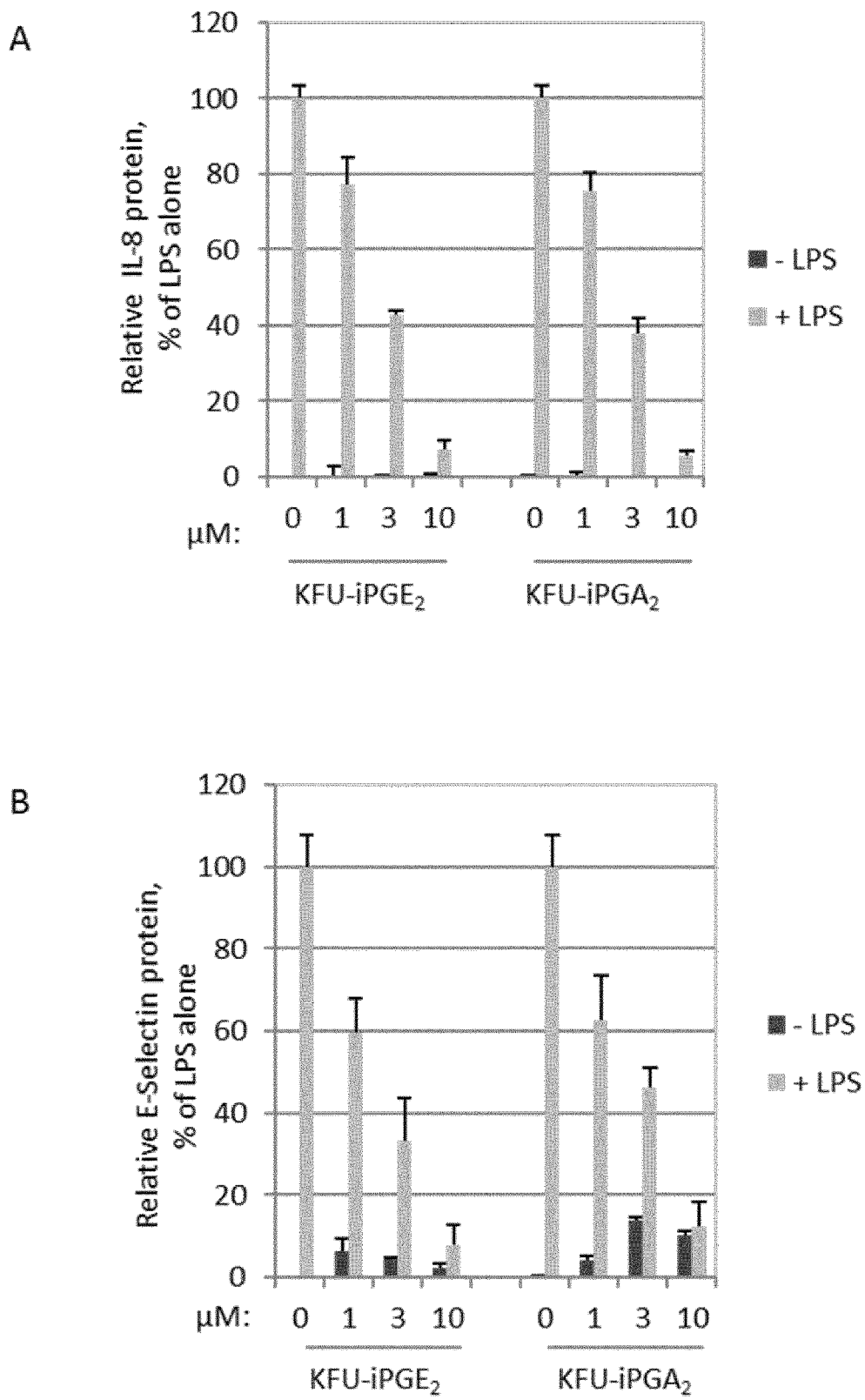
FIG. 1 shows human endothelial cells which were stimulated with LPS in the presence of increasing concentrations of prostanoids bound to compound (7) (i.e. compounds (III) "KFU-iPGE2" of example 7 and (VI) "KFU-iPGA2" of example 11). After 6 hours expression of proinflammatory chemokine IL-8 in the medium (A) and proinflammatory adhesion molecule E-selectin on the cell surface (B) were determined using an immune assay (ELISA).

In vitro-oxidized phospholipids (OxPLs) (Bochkov V N et al. Antioxid. Redox Signal. (2010); 12:1009-1059) are increasingly recognized for their anti-Toll-like receptor and lung endothelial barrier-protective activities in vitro and in vivo. However, the vast majority of these results were obtained using complex mixtures of OxPLs generated by oxidation of common, physiological phospholipids. Such natural OxPLs are ineffective for in vivo therapy for three important reasons. First, natural OxPLs are rapidly degraded by phospholipases A. Second, natural OxPL mixtures contain a large proportion of oxidatively fragmented molecular species that are toxic and disrupt lung endothelial barrier. In addition, chemical attachment of oxidized polyunsaturated fatty acids to the natural phospholipid scaffold is technically difficult, which complicates synthesis of individual active compounds. The present invention provides a solution to overcome the aforementioned drawbacks by providing a modified phospholipid-like scaffold that is resistant to phospholipases, for instance, and allows simple attachment of oxidized residues through an amide group or through an ether group, whereby an amide group is particularly preferred. This approach allows synthesizing individual compounds capable of inhibiting the activation of Toll-like receptors, for instance Toll-like receptors 2 and 4 activatable by components of Gram-positive and Gram-negative bacteria, and at the same time protecting surprisingly endothelial barrier in lung vessels. Hence, such compounds may be especially effective in prevention of lung complications of sepsis, in particular of lethal sepsis, and systemic inflammation. The compounds of the present invention enhance endothelial barrier in lung vessels, reverse action of edemagenic mediators and prevent formation of lung edema in vivo.

It has been found by the inventors that a compound having a structure according to formula (I)

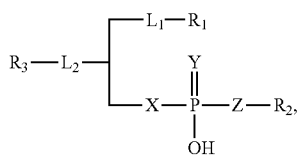

(I)

or salts thereof, wherein $R_1$ is a branched or linear alkyl, acyl, alkenyl, hydroxyalkyl, hydroxyalkenyl, or hydroxy-alkinyl residue comprising 6 to 30 carbon atoms, $R_2$ is selected from the group consisting of
a) an alkyl residue comprising 1 to 10 carbon atoms and comprising a terminal or cyclic quaternary ammonium,
b) an alkyl residue comprising 1 to 10 carbon atoms and comprising a terminal amino group and/or 1 to 3 hydroxyl groups,
c) an amino acid residue,
d) a five or six carbon sugar and
e) H, $R_3$ is a residue selected from the group consisting of an alkyl, alkenyl, prostanyl-dialkyl, furanyl-dialkyl, cyclobutyl-dialkyl, cycloalkyl and aryl group of 2 to 40 carbon atoms length and comprising at least one keto group, epoxy group, aldehyde group, peroxy group, hydroperoxy group, hydroxyl group or a free carboxyl group, L1 is selected from the group consisting of O, S, $CH_2$,

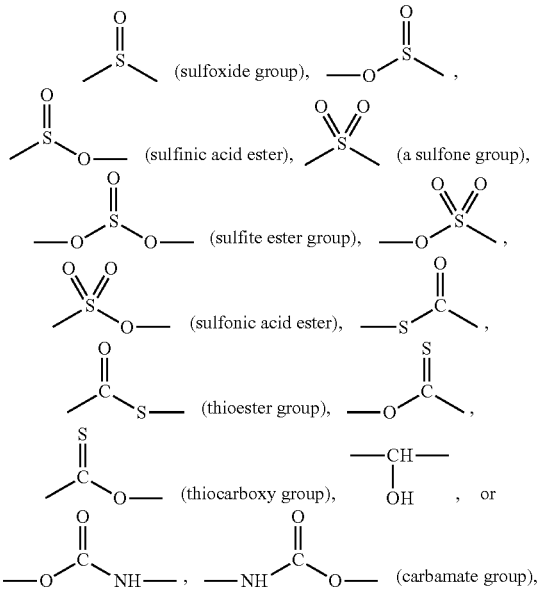

L2 is an amide group

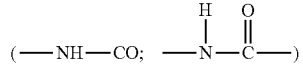

or an ether group

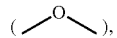

X and Z are independently O, S or CH2, and

Y is selected from the group consisting of O and S, is a stable compound which is not or substantially not degraded by phospholipases, in particular phospholipases A and B, for instance, and which has anti-inflammatory properties by inhibiting the activation of Toll-like receptors and exhibits endothelial barrier protecting effects.

In order to enhance the resistance of the compound of the present invention towards phospholipases even more X, Y and/or Z are preferably not O (oxygen). In such a case X, and Z are preferably S or $CH_2$, Y is preferably S.

R1 of formula (I) is an alkyl, alkenyl, hydroxyalkyl, or hydroxy-alkinyl residue, most preferably an alkyl residue, comprising 2 to 30, preferably 2 to 28, more preferably 2 to 26, more preferably 2 to 24, more preferably 2 to 22, more preferably 2 to 20, more preferably 2 to 18, carbon atoms, which is optionally substituted by 1 to 10, preferably 1 to 5, more preferably 1 to 3, more preferably 1 or 2, substituents independently selected from the group consisting of alkyl and alkenyl comprising 1 to 5 carbon atoms. R1 of formula (I) is particularly preferred an unsubstituted alkyl residue as defined above.

An "alkyl" residue, as used herein, refers to a saturated aliphatic hydrocarbon chain.

An "alkenyl" residue, as used herein, refers to an unsaturated aliphatic hydrocarbon chain comprising at least two carbon atoms and at least one carbon-carbon double bond. In a preferred embodiment of the present invention the alkenyl group comprises one, two, three, four, five or six double bonds, wherein each double bond is formed between two carbon atoms. The "alkenyl" residue of the present invention may also comprise one or more carbon-carbon triple bonds, provided that the number of these carbon-carbon triple bonds is lower than the number of carbon-carbon double bonds.

An "alkinyl" residue, as used herein, refers to an unsaturated aliphatic hydrocarbon atom comprising at least two carbon atoms and at least one carbon-carbon triple bond. In a preferred embodiment of the present invention the alkinyl group comprises one, two, three, four, five or six triple bonds, wherein each triple bond is formed between two carbon atoms. The "alkinyl" residue of the present invention may also comprise one or more carbon-carbon double bonds, provided that the number of these carbon-carbon double bonds is lower than the number of carbon-carbon triple bonds.

The alkyl, alkenyl and alkinyl residues may also comprise one more hydroxy (—OH) groups attached to one or more carbon atoms. In a preferred embodiment of the present invention such alkyl, alkenyl and alkinyl residues, called hydroxyalkyl, hydroxyalkenyl and hydroxyalkinyl, respectively, comprise at least one, preferably at least two, more preferably at least three, more preferably at least four, more preferably at least five, hydroxy groups.

An "acyl" residue, as used herein, refers to a saturated or unsaturated aliphatic hydrocarbon chain which comprises at least one acyl group, preferably one, two, three, four or five acyl groups, at any position of the residue.

One or more of hydrogen atoms of the alkyl, alkenyl, hydroxyalkyl and hydroxyl-alkinyl residues R1 of formula (I) may be substituted by 1 to 10, preferably 1 to 8, more preferably 1 to 6, more preferably 1 to 4, more preferably 1 to 3, more preferably 1 or 2 or in particular 1 substituent independently selected from the group consisting of alkyl and alkenyl comprising 1 to 5, preferably 1 to 4, more preferably 1 to 3, more preferably 1 to 2 or more preferably 1 carbon atom. The substitution of one or more of said hydrogen atoms results in the formation of substituted, i.e. branched, alkyl, alkenyl and acyl residues.

The term "substituted", as used herein, refers to moieties having substituents replacing a hydrogen on one or more carbon atoms of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds, in particular those explicitly mentioned herein.

In a particular preferred embodiment of the present invention R1 is an unsubstituted and optionally linear alkyl residue comprising 2 to 30 carbon atoms as defined above, whereby this alkyl residue comprises preferably 14, 16 or 18 carbon atoms, in particular 16 carbon atoms.

In a preferred embodiment of the present invention R1 of formula (I) is a residue selected from the group consisting of hexyl residue, heptyl residue, octyl residue, nonyl residue, decyl residue, undecyl residue, dodecyl residue, tetradecyl residue, hexadecyl residue and octadecyl group, preferably a hexadecyl group. One or more hydrogen atoms of these residues may be independently substituted as defined above.

$R_2$ of formula (I) is selected from the group consisting of a) an alkyl residue comprising 1 to 10 carbon atoms and comprising a terminal quaternary ammonium or amino group and/or 1 to 3, preferably 1, 2 or 3, hydroxyl groups b) a substituted or unsubstituted linear or cyclic homoalkyl or heteroalkyl residue comprising 2 to 8 carbon atoms, preferably substituted with hydroxyl and/or phosphate groups (e.g. at least 1, 2, 3, 4 or 5), and c) aminoacids, and d) H.

The alkyl residue R2 of formula (I) comprising a terminal quaternary ammonium or amino residue may comprise 1 to 8, preferably 1 to 6, more preferably 1 to 5, more preferably 1 to 4, more preferably 1 to 3, more preferably 1 or 2, or even 1 carbon atom. At least one of the carbon atoms of the alkyl residue R2 may be substituted with a quaternary ammonium residue, in particular a terminal carbon atom thereof.

The term "quaternary ammonium residue", as used herein, refers to a residue containing at least one nitrogen atom carrying a positive electric charge, which nitrogen atom is bonded only to carbon atoms, preferably of alkyl residues comprising 1 to 5 carbon atoms, preferably 1 or 2 carbon atoms.

According to a preferred embodiment of the present invention the alkyl residue comprising 1 to 10 carbon atoms and comprising at least one quaternary ammonium residue attached thereto is a choline residue.

Choline is a quaternary ammonium residue and can be part of phospholipids, in particular of phosphatidylcholine and sphingomyelin, which are contained in cell membranes of mammals. Compounds of the present invention which comprise a choline residue at R2 are particularly preferred.

Alkyl residue R2 can be comprised of 2 to 8 carbon atoms (C2: ethanol), or additionally contain one terminal amino group (C2: ethanolamine), an amino and a carboxyl group (C3: serine), one hydroxy and one amino groups (C3: serinol), two hydroxyl groups (C3: glycerol), cyclohexyl group with 5 substituted hydroxy groups (inositol), or be a hydrogen (the entire structure will be phosphatidic acid).

R3 of formula (I) can be a substituted or unsubstituted linear or cyclic homoalkyl or heteroalkyl residue comprising 3 to 8 carbon atoms.

Alkyl residues that are limited to hydrocarbon groups are termed "homoalkyl". Such residues may comprise substituted hydrogen atoms.

The term "heteroalkyl", as used herein, refers to a stable straight- or branched-chain or cyclic alkyl residue consisting of the stated number of carbon atoms and at least one heteroatom selected from the group consisting of O, N, and S, wherein the heteroatom may optionally be oxidized. One or more heteroatoms may be placed at any internal position of the heteroalkyl residue or at a terminus of the chain. "Heteroalkyl" residues may comprise substituted hydrogen atoms.

According to a preferred embodiment of the present invention this cyclic alkyl residue can be cyclopentane or cyclohexane, which can be optionally substituted by 1 to 3 alkyl residues comprising 3 to 10 carbon atoms. Both of these residues can be optionally substituted with at least one, hydroxyl or keto groups.

According to a particularly preferred embodiment of the present invention the linear or cyclic homoalkyl or heteroalkyl residue comprising 3 to 10 carbon atoms is substituted with at least one hydroxy group, keto group, epoxy group, endoperoxy group or hydroperoxy group and/or comprises a terminal carboxy group. The heteroalkyl residue may contain O or S within the structure.

It turned out that the compound of the present invention has to comprise at R3 of formula (I) oxygen-containing groups such as keto, aldehyde or hydroxyl groups. The presence of such groups is advantageous for the compound's capability to inhibit activation of Toll-like receptors, in particular of Toll-like receptors 2 and 4. The same or at least a similar effect that is observable with oxidized phospholipids (OxPLs). As mentioned above the compounds of the present invention exhibit surprisingly also endothelial barrier protecting effects in, for instance, lung vessels. Therefore, R3 of formula (I) is a residue comprising an alkyl, alkenyl, prostanyl-dialkyl, (iso)furanyl-dialkyl, cycloalkyl and/or aryl group comprising 1 to 40 carbon atoms and additionally comprising at least one, preferably at least two, more preferably at least three, more preferably at least four, more preferably at least five, more preferably at least six, keto groups, aldehyde groups, carboxy groups, peroxy groups, hydroperoxy groups or hydroxyl groups. R3 may comprise oxygen-containing groups of the same type or different types. Furthermore, R3 of formula (I) is preferably an alkenyl residue comprising one or more carbon-carbon double bonds as defined above.

R3 of formula (I) is preferably an oxylipin, preferably selected from the group consisting of prostaglandins, isoprostanes, lipoxins, resolvins, protectins and maresins, monohydroxy-, dihydroxy-, trihydroxy-, tetrahydroxy fatty acid residues with epoxy-, keto-, hydroperoxy-, hydroxyl- or prostane groups independent on regio- and stereo-position of oxygen-containing groups within their structures as defined above. The prostaglandin is preferably selected from the group consisting of prostacyclins, prostaglandins, isoprostanes, lipoxins, maresins, resolvins and protectins. All the oxylipin structures mentioned herein are well known to a person skilled in the art and may be naturally occurring (Serhan C N, Chiang N, Dalli J, Levy B D. Lipid mediators in the resolution of inflammation. Cold Spring Harb Perspect Biol. (2014) 30; 7(2):a016311; Serhan C N. Pro-resolving lipid mediators are leads for resolution physiology. Nature. (2014);510(7503):92-101; Milne G L, Dai Q, Roberts L J $2^{nd}$. The isoprostanes-25 years later. Biochim Biophys Acta. (2015);1851(4):433-45). Of course the oxylipins mentioned and claimed herein can be derivatives or analogs of naturally occurring oxylipins such as those containing e.g. sulfur or nitrogen atoms.

R3 of formula (I) of the present invention may also be a residue which exhibits pharmacological activity.

The prostacyclin analog is preferably selected from the group consisting of 5-{(E)-(1S,5S,6R,7R)-7-hydroxy-6[(E)-(3S,4RS)-3-hydroxy-4-methyl-1-octen-6-inyl]-bicyclo [3.3.0]octan-3-ylidene}pentanyl (iloprost), and residues of 5-cis-iloprost, 5-cis-15(R)-iloprost, 15(R)-iloprost, 15-keto-iloprost, carbaprostacyclin, 5-cis-carbaprostacyclin, 13,14-dehydro-15-cyclohexyl, 5Z-[3aR,3-difluorohexahydro-5R-hydroxy-4R-[3R-hydroxy-4S-methyl-1E-nonen-6aS-ynyl]-2H-cyclopenta[b]furan-2-ylidene]-pentanoyl (16(R)-AFP 07), 5Z-[(3aR,4R,5R,6aS)-3,3-difluorohexahydro-5-hydroxy-4-[(1E,3S,4S)-3-hydroxy-4-methyl-1-nonen-6-ynyl]-2H-cyclopenta[b]furan-2-ylidene]-pentanoyl (AFP07), treprostinil, cicaprost, beraprost, ciprostene and 15(R)-prostaglandin $I_2$.

L1 of the compound having formula (I) is preferably selected from the group consisting of O, S and CH2, whereby O is particularly preferred, which is naturally occurring at this position in phospholipids, for instance.

In order to increase the stability of the compounds of the present invention, in particular in regard to enzymatic degradation (in vivo) (for instance by phospholipases), L2 is in a particularly preferred embodiment of the present invention an amide or ether group. The presence of an amide group at this position prevents or at least reduces the degradation of the compounds of the present invention. The increased stability has the advantage that the biological/pharmacological activity of the compounds of the present invention lasts significantly longer than those of oxidized phospholipids which are much more unstable. Furthermore, the provision of an amide bond might also have an influence on the biological activity of the compounds of the present invention in relation to the inhibitory activity of Toll-like receptors and, in particular, on the protection of endothelial barriers.

X and Z are independently O, S or $CH_2$, whereby it is particularly preferred that X and Z are O.

Y is selected from the group consisting of O or S, whereby it is particularly preferred that Y is O.

According to a preferred embodiment of the present invention the compound of the present invention may have a structure according formula (Ia):

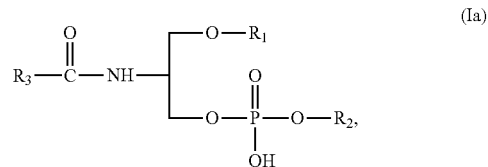

whereby substituents R1, R2 and R3 are those as disclosed and described above.

The compounds of the present invention having formula (I) or (Ia) may be provided in the form of a salt. Particularly preferred are pharmaceutically acceptable salts of the compound of the present invention. These pharmaceutically acceptable salts comprise pharmaceutically acceptable cations selected from the group including but not limited to sodium, potassium, magnesium, ammonium, triethylammonium.

Another aspect of the present invention relates to a method for synthesizing the compound of the present invention as defined above and having a structure according to formula (I) or (Ia).

The synthesis of a compound having a structure according to formula (I) or (Ia) can be achieved using conventional methods regularly used in organic chemistry and well known to a person skilled in the art.

In detail, in a first step of the synthesis the amino group of an 1-O(R1)-2-deoxy-2-amino-sn-glycerol (1), where R1 is an residue free of hydroxyl groups, is protected. This can be achieved by using, for instance, di-tert-butyl dicarbonate ($Boc_2O$) forming a tert-butyl (Boc) protecting group by in the presence of triethylamine in dichloromethane (see Scheme A). The free hydroxyl group at the sn-3 position of the resulting protected glycerol (2) derivative can then be phosphytilated by reaction with bis(diisopropylamino)(2-cyanoethoxy)-phosphine in the presence of a diisopropylamino tetrazole as an activator in water-free dichloromethane, for instance. The phosphytilated product (3) was used for further reaction with choline tosylate in the presence of tetrazole as a catalysator. Afterwards, the obtained phosphite (4) can be oxidized by tert-butyl hydroperoxide to yield the phosphate (5). The oxidation can also be performed using 0.1M iodine in THF/water/pyridine 7:2:1 (v/v/v) as described in WO1999067378A1. Alternatively, oxidation of (4) can be achieved under action of atomatic sulfur ($S_8$) to obtain the thioate (5) with Y=S. The cyanoethyl protective group of (5) was further removed under action of triethylamine. The Boc-protective group in the resulted (6) was cleaved in the presence of trifluoracetic acid to give (7).

Compound (I) with Y=S can be synthesized from (4) by using elemental sulfur ($S_8$) as an oxidizing agent instead of tert-butyl hydroperoxide as described in Bruzik K S (J. Chem. Soc. Perkin Trans. 1988, 1:423-431).

Compound (I) with Z=S can be synthesized using a method described in Bushnev et al. (Bioorg. Med. Chem. 1994, 2(3):147-51).

Compound (I) with X=S can be prepared using a method described by by Hendrickson H S et al. (Chem. Phys. Lipids 1996, 84:87-92).

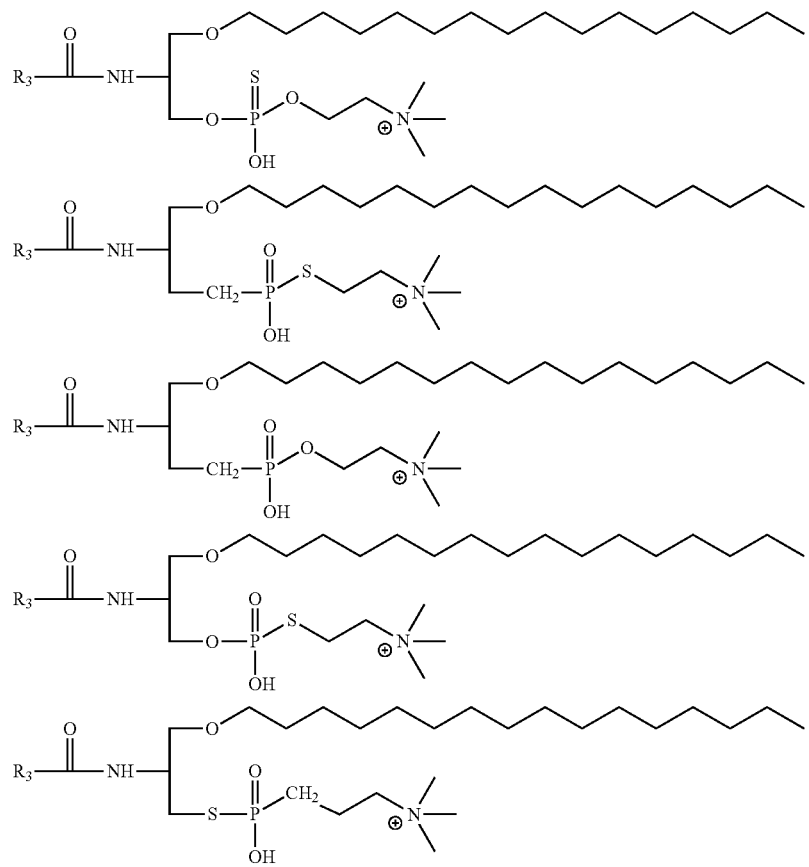

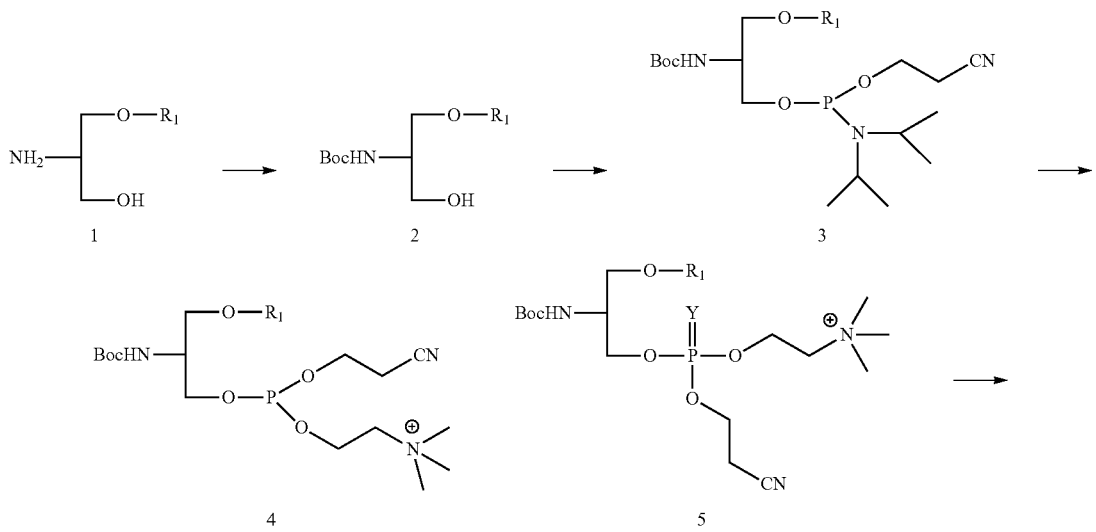

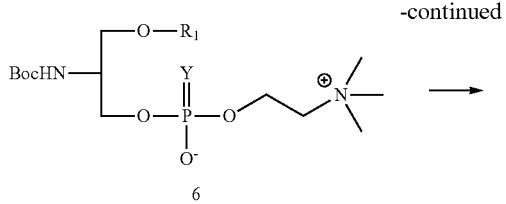
6

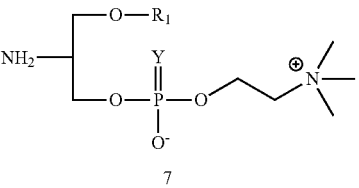
7

The obtained scaffold (7) is further used for preparation of an oxidized phospholipid analogs as follows. Any (fatty) acid containing the free carboxylic group (8) is first activated to the respective succinimide ester under action of N-hydroxysuccinimide and a coupling reagent, preferably EDC.

Other coupling reagents (carbodiimide derivatives) can be used: e.g. dicyclohexylcarbodiimide, diisopropylcarbodiimide, N-cyclohexyl-N'-(2-morpholinoethyl)carbodiimid-methyl-p-toluolsulfonat or their polymer-bound derivatives. EDC is preferred as it is water-soluble and therefore the excess of it or its degradation product can be easily removed by liquid-liquid extraction, for example by Folch extraction. If the reaction with formation of succinimide ester (9) from (8) is complete, the separation of EDC and its degradation product by simple extraction is advantageous, since the succinimide ester (9) is water insoluble and can be obtained in a pure form without any additional purification steps.

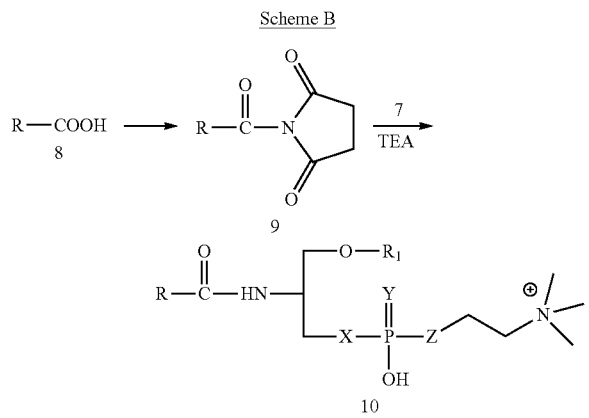

The obtained succinimide ester (9) can be easily used for acylation of the free amino group in (7, KFU) in the presence of mild amines, like triethylamine.

The obtained compound (10) can be easily purified by solid-phase extraction on columns with reversed phase (e.g. SPE-C18) using a gradient of methanol (ethanol or acetonitrile) in water.

The structure (7) is used like on the LEGO-principle: to the ground structure (7) several types of fatty acid residues can be attached. The advantage of this method is that in such a reaction sequence numerous phospholipids with different sn-2 residues can be obtained under very mild conditions and this allows attaching even chemically labile compounds (e.g., prostaglandins, isoprostanes etc).

Another aspect of the present invention relates to a pharmaceutical composition comprising a compound according to the present invention.

The compounds of the present invention can formulated as a pharmaceutical preparation which can be administered to a mammal, in particular to a human.

The compound of the present invention can be directly used as a medicament or as part of a pharmaceutical composition or pharmaceutical formulation by mixing the compound with at least one pharmaceutically acceptable excipient by means known in the art and generally used in a production method of pharmaceutical preparations. Each excipient must be "acceptable" in the sense of being compatible with the other ingredients of the preparation and not injurious to the mammal receiving the pharmaceutical preparation of the present invention.

The pharmaceutical preparation of the present invention can be orally or parenterally administered to mammals, in particular to humans, but also to animals like monkeys, cows, horses, pigs, mice, rats, cats, dogs, sheep or goats.

The pharmaceutical preparation of the present invention may be provided in the form of tablet (including sugar-coated tablet, film-coated tablet, sublingual tablet, orally disintegrating tablet, buccal and the like), pill, powder, granule, capsule (including soft capsule, microcapsule), syrup, liquid, emulsion, suspension, release control preparation (e.g., immediate-release preparation, sustained-release preparation, sustained-release microcapsule), aerosol, film (e.g., orally disintegrating film, oral mucosa-adhesive film), injection (e.g., subcutaneous injection, intravenous injection, intramuscular injection, intraperitoneal injection), drip infusion, transdermal absorption type preparation, ointment, lotion, adhesive preparation, suppository (e.g., rectal suppository, vaginal suppository), pellet, nasal preparation, pulmonary preparation (inhalant), eye drop and the like, orally or parenterally (e.g., intravenous, intramuscular, subcutaneous, intraorgan, intranasal, intradermal, instillation, intracerebral, intrarectal, intravaginal, intraperitoneal and intratumor administrations, administration to the vicinity of tumor, and direct administration to the lesion). Depending on the disease or disorder to be treated the pharmaceutical preparation of the present invention is particularly preferred provided in the form of a pulmonary preparation (for inhalation) for treating pulmonary diseases and disorders and in the form of an injection for treating sepsis and related diseases and disorders.

The content of the compound of the present invention in the pharmaceutical preparation of the present invention is about 0.01 to 100% by weight of the entire pharmaceutical preparation. The dose of the compound of the present invention to be administered to a mammal varies depending on the subject of administration, administration route, disease and the like. A physician or veterinarian having ordinary skill in the art can readily determine and prescribe the therapeutically effective amount of the pharmaceutical composition or the compound of the present invention, respectively, required. For example, the physician or veterinarian could start doses of the pharmaceutical composition or compound at levels lower than that required in order to achieve the desired therapeutic effect and gradually increase the dosage until the desired effect is achieved. By "therapeutically effective amount" is meant the concentration of a compound that is sufficient to elicit the desired therapeutic effect. Methods to determine efficacy and dosage are known to those skilled in the art.

In general, a suitable daily dose of an active compound used in the compositions and methods of the invention will be that amount of the compound that is the lowest dose effective to produce a therapeutic effect. Such an effective dose will generally depend upon the factors described above. If desired, the effective daily dose of the active compound may be administered as one, two, three, four, five, six or more sub-doses administered separately at appropriate intervals throughout the day, optionally, in unit dosage forms. In certain embodiments of the present invention, the active compound may be administered two or three times daily. In preferred embodiments, the active compound will be administered once daily.

The pharmaceutical preparation of the present invention may comprise one or more excipients like a pharmaceutically acceptable carrier. Further excipients include lubricants, binding agents and disintegrants for solid preparations like tablets; or solvents, solubilizing agents, suspending agents, isotonic agents, buffering agents, soothing agents and the like for liquid preparations. Furthermore, when necessary, ordinary additives such as preservatives, antioxidants, colorants, sweetening agents, adsorbing agents, wetting agents and the like can be also used as appropriate in an appropriate amount.

Examples of excipients include lactose, white sugar, D-mannitol, starch, corn starch, crystalline cellulose, light anhydrous silicic acid and the like.

Examples of lubricants include magnesium stearate, calcium stearate, talc, colloidal silica and the like.

Examples of binding agents include crystalline cellulose, white sugar, D-mannitol, dextrin, hydroxypropylcellulose, hydroxypropylmethylcellulose, polyvinylpyrrolidone, starch, sucrose, gelatin, methylcellulose, carboxymethylcellulose sodium and the like.

Examples of disintegrants include starch, carboxymethylcellulose, carboxymethylcellulose calcium, carboxymethylstarch sodium, L-hydroxypropylcellulose and the like.

Examples of solvents include water for injection, alcohol, propylene glycol, Macrogol, sesame oil, corn oil, olive oil and the like.

Examples of solubilizing agents include polyethylene glycol, propylene glycol, D-mannitol, benzyl benzoate, ethanol, trisaminomethane, cholesterol, triethanolamine, sodium carbonate, sodium citrate and the like.

Examples of the suspending agents include surfactants such as stearyl triethanolamine, sodium lauryl sulfate, laurylaminopropionic acid, lecithin, benzalkonium chloride, benzetonium chloride, glycerin monostearate and the like; hydrophilic polymers such as polyvinyl alcohol, polyvinylpyrrolidone, carboxymethylcellulose sodium, methylcellulose, hydroxymethylcellulose, hydroxyethylcellulose, hydroxypropylcellulose and the like; and the like.

Examples of the isotonic agents include glucose, D-sorbitol, sodium chloride, glycerin, D-mannitol and the like.

Examples of buffering agents include buffer solutions such as phosphates, acetates, carbonates, citrates and the like.

Examples of soothing agents include benzyl alcohol and the like.

Examples of preservatives include parahydroxybenzoates, chlorobutanol, benzyl alcohol, phenylethyl alcohol, dehydroacetic acid, sorbic acid and the like.

Examples of antioxidants include sulfites, ascorbic acid, alpha-tocopherol and the like.

Tablets may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active and/or dispersing agent. Molded tablets may be made by molding in a suitable machine a mixture of the powdered compound moistened with an inert liquid diluent.

The tablets, and other solid dosage forms of the pharmaceutical compositions, such as dragees, capsules (including sprinkle capsules and gelatin capsules), pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms useful for oral administration include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

As mentioned above the compounds and pharmaceutical compositions of the present invention may be used for treating an inflammatory disease like sepsis or disorder or a disease associated with Toll-like receptor 2 (TLR2) and/or Toll-like receptor 4 (TLR4) (Molteni M, Gemma S, and Rosetti C. Mediators Inflamm. 2016, Article ID 6978936, 9 pages; Pandolfi F, Altamura S, Frosali S, Conti, Clin Ther. 2016, 38(5):1017-28; Liu Y, Yin H, Zhao M, and Lu Q. Clin. Rev. Allergy Immunol. 2014, 47(2):136-47). These disorders may include acute lung injury, pulmonary fibrosis, stroke, non-alcoholic steatohepatitis, inflammatory bowel disease, neuroinflammatory diseases, organ infarction, brain injury and trauma. It has been shown that knock-out of TLR2 or TLR4 genes leads to amelioration of these pathological conditions. Such diseases and in particular the conditions mentioned below are unified by activation of TLR4/TLR2 signaling and/or activation of NFkB inflammatory cascade by bacterial pathogens or endogenous factors such as danger associated molecular patterns (DAMPs) (Khakpour S, Wilhelmsen K, Hellman J. Innate Immun. 2015, 21(8):827-846; Reuven E M, Fink A, Shai Y. Biochim Biophys Acta 2014, 1838(6):1586-1593). Both, TLR-dependent and TLR-independent activation of NFkB inflammatory cascade can be inhibited by the compounds of the present invention having formula (I) or (Ia) as defined herein.

Therefore, the present invention relates also to a method for treating an inflammatory disease or disorder or a disease or disorder associated with Toll-like receptor 2 (TLR2) and/or Toll-like receptor 4 (TLR4) and/or NFkB inflammatory cascade comprising the administration of a compound or a pharmaceutical composition according to the present invention to a mammal, most preferably human, in need thereof.

As mentioned above the compounds of the present invention inhibit TLR-dependent and TLR-independent activation of NFkB inflammatory cascade, which allows the treatment of inflammatory diseases or disorders or diseases or disorders associated with Toll-like receptor 2 (TLR2) and/or Toll-like receptor 4 (TLR4).

The compound of the present invention can be used in the treatment or prevention of diseases and disorders associated with Toll-like receptor 2 (TLR2) and/or Toll-like receptor 4 (TLR4) and/or NFkB inflammatory cascade in any mammal including humans. However, it is particularly preferred to administer the compound or pharmaceutical preparation of the present invention to humans, monkeys, cattle, horses, pigs, mice, rats, cats, dogs, sheep and/or goats, whereby humans, cattle and horses are particularly preferred.

The term "treating", as used herein, refers to the stabilization of a disease, disorder or condition, i.e., arresting its development; and relieving one or more symptoms of the disease, disorder or condition, i.e., causing regression of the disease, disorder and/or condition. In an ideal situation "treating" results in curing entirely a mammal from a disease.

In the course of the treatment the compound is administered to a mammal in an effective amount resulting at least in an amelioration of the disease or disorder. In order to achieve a treatment the effective amount to be administered may vary depending on several factors like kind of disease or disorder, progress of disease or disorder, route of administration, age and sex of the mammal to be treated, etc. Generally speaking, however, the compound of the present invention can be administered to a patient in an effective amount greater than 10 ng per day per kg body weight, preferably greater than 20 ng per day per kg body weight, more preferably greater than 30 ng per day per kg body weight, more preferably greater than 50 ng per day per kg body weight, more preferably greater than 100 ng per day per kg body weight, more preferably greater than 150 ng per day per kg body weight, more preferably greater than 200 ng per day per kg body weight, more preferably greater than 500 ng per day per kg body weight, and up to 10 mg per day per kg body weight, preferably up to 5 mg per day per kg body weight, more preferably up to 2 mg per day per kg body weight, more preferably up to 1 mg per day per kg body weight, more preferably up to 0.5 mg per day per kg body weight, more preferably up to 0.1 mg per day per kg body weight, more preferably up to 50 µg per day per kg body weight, more preferably up to 10 µg per day per kg body weight.

In certain embodiments of the present invention the compound of the present invention is administered to a patient in an effective amount from 10 ng to 10 mg per day per kg body weight, preferably from 20 ng to 5 mg per day per kg body weight, more preferably from 30 ng to 2 mg per day per kg body weight, more preferably from 50 ng to 1 mg per day per kg body weight, more preferably from 100 ng to 0.5 mg per day per kg body weight, more preferably from 150 ng to 0.1 mg per day per kg body weight, more preferably from 200 ng to 50 µg per day per kg body weight, more preferably from 500 ng to 10 µg per day per kg body weight.

In certain embodiments, the compound or the pharmaceutical preparation of the present invention may be administered over the course of a day through any suitable dosing regimen. Suitable dosing regimens may include once daily dosing, twice daily dosing, three times daily dosing, four times daily dosing, five times daily dosing, and any other suitable dosing regimen, such that the net effect throughout the course of the day is administering the total dosages per day as set forth above.

In certain other embodiments of the present invention, suitable dosing regimens further include once every two days dosing, such as every other day, or once every three days dosing, such as every third day, such that the net effect throughout the course of the day of dosing is administering at least the total dosages per day of the compound of the present invention as set forth above.

EXAMPLES

Chemical Syntheses
Materials:
12-Hydroxydodecanoic acid, N-hydroxysuccinimide, water-free tetrahydrofuran supplemented with butylated hydroxy toluene, water-free dichloromethane, 4-dimethylamino pyridine, BOC anhydride, 0.45 M tetrazole solution in acetonitrile, tert-butyl hydroperoxide (~5.5 M in decane), DSC-C18 SPE columns (100 mg, 1 ml) were purchased from Sigma-Aldrich (USA). 1-Ethyl-3-(3-dimethylaminopropyl)carbodiimid hydrochloride (EDC), water were from Thermo Fisher Scientific (USA). Prostaglandins, isoprostanes, and iloprost were purchased from Cayman Chemicals (USA). 1-O-Hexadecyl-2-deoxy-2-amino-sn-glycerol was from Bachem A G (Switzerland). Chloroform, ethanol and methanol were from VWR International (USA). Lipid A, Pam3CSK4, and FSL-1 were from InvivoGen (France).

TLC, Mass Spectrometry and Determination of Phospholipid Concentrations:

Thin layer chromatography (TLC) was performed on Kieselgel 60 TLC plates (VWR International) in A) chloroform-methanol (10:1, v/v) or B) chloroform-methanol-water (100:50:10, v/v/v) followed by the deeping the plate into a solution of 10% $CuSO_4$ in 8.5% $H_3PO_4$ and consequent heating to 120° C. Mass-spectra of synthetic compounds were recorded on LTQ-XL ion-trap mass-spectrometer at voltage of 1.9 kV, capillary temperature of 200° C. and capillary voltage of 45V. The samples were dissolved in 80% MeOH supplemented with 1% formic acid (Fluka). Spectra of synthetic phospholipids were recorded in positive mode in the range of m/z values between 200 and 2000. Synthetic phospholipids were dissolved in chloroform and stored at −70° C. Phospholipid concentrations were determined as described previously (Broekhuyse R M. Biochim. Biophys. Acta 152(1968): 307-315).

Example 1: Synthesis of 1-O-Hexadecyl-2-deoxy-2-amino-sn-glycero-phosphocholine (7) as a Scaffold for Modified Phospholipids General Description The amino group of 1-O-hexadecyl-2-deoxy-2-amino-sn-glycerol (1) was protected with a tert-butyl (Boc) protecting group by reaction with di-tert-butyl dicarbonate in the presence of triethylamine in dichloromethane (see Scheme 1). The free 3-OH group of the resulting protected glycerol (2) derivative was then phosphytilated by reaction with bis(diisopropylamino)(2-cyanoethoxy)-phosphine in the presence of a diisopropylaminotetrazole as an activator in water-free dichloromethane. The phosphytilated product (3) was isolated by flash chromatography on silica gel with a 84.8% yield. The following sequential reactions were performed as one-pot reactions and monitored by TLC: 1) condensation with choline tosylate in the presence of tetrazole giving (4), 2) oxidation of phosphorus(III) to phosphorus(V) by tert-butylhydroperoxide to give (5), and 3) cleavage of the 2-cyanoethyl protecting group at phosphorus by triethylamine to give (6). After purification, 2-Boc-amino-3-phosphocholine (6) was obtained with 60.0% yield. The deprotection of the amino-group in (6) by trifluoracetic acid led to 1-O-hexadecyl-2-deoxy-2-amino-sn-glycero-3-phosphocholine (7), the "scaffold" compound, which was further used for syntheses of prostaglandin-like phospholipids.

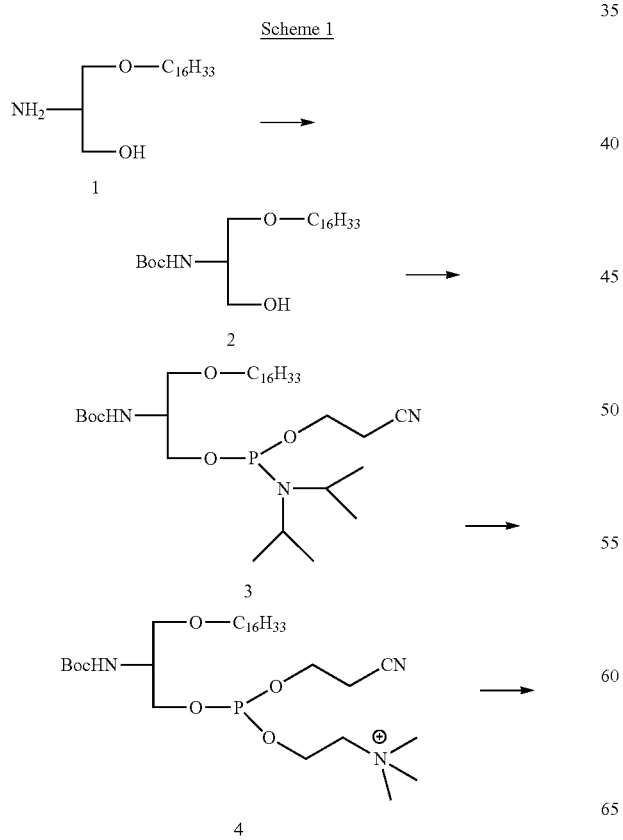

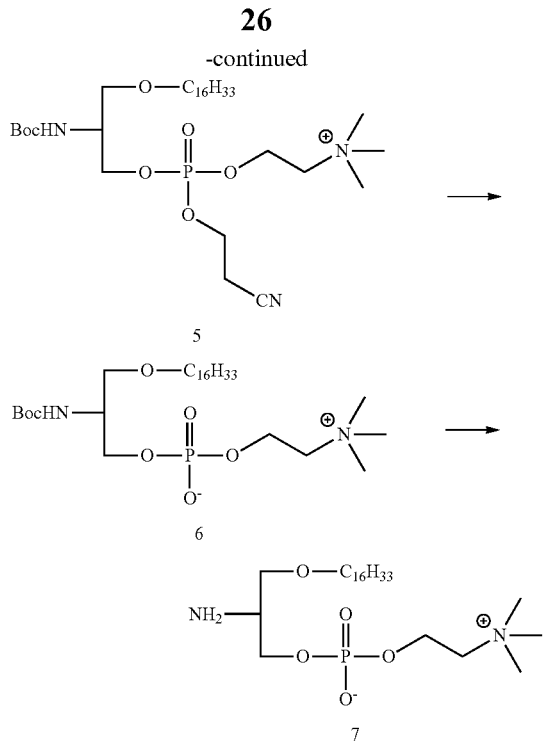

The general procedure for synthesis of prostaglandin-like phospholipids included 2 steps (Scheme 2).

First, prostaglandin, isoprostaglandin or any other (hydroxy)fatty acid (8) was activated by a reaction with N-hydroxysuccinimide in the presence of EDC in dichloromethane. The resulted succinimide ester (9) was extracted with chloroform-methanol or dichlormethane-methanol according to a Folch method and used further without any additional purification. Second, equimolar amounts of a succinimide ester (9) and the KFU (7) were mixed in the presence of triethylamine and let react under argon atmosphere overnight. The acylated PL product (10) was purified on a C18-SPE column using a gradient of methanol (or ethanol) in water depending on polarity of the product. The purity was confirmed by TLC and MS. Concentrations of phospholipids were determined by a phosphorus microassay as described above.

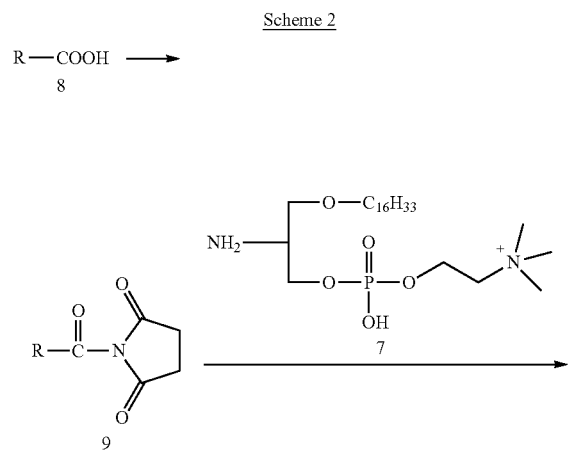

-continued

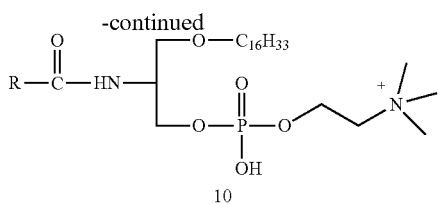

10

Example 2: Synthesis of 1-O-Hexadecyl 2-deoxy-2-(tert-butoxycarbonyl)amino-sn-glycerol (2)

To a solution of 1-O-hexadecyl-2-deoxy-2-amino-sn-glycerol (1) (32.0 mg, 101.4 µmol) in 3 ml dichloromethane, 26.16 µl of di-tert-butyl dicarbonate (Boc ahydride, 111.6 µmol) and 10 µl of triethylamine (TEA, Sigma-Aldrich) were added. After 4 hrs the reaction was complete as analyzed by TLC. The mixture was evaporated under stream of argon and applied onto a silica gel column. The product (2) was eluted with a gradient from 0% to 5% of MeOH in chloroform. Fractions containing the product were collected and evaporated under argon. Yield: 41.2 mg (98%). Rf (system A): 0.81.

Example 3: Synthesis of 1-O-Hexadecyl2-deoxy-2-(tert-butoxycarbonyl)amino-sn-glycero-phosphoamidite (3)

The phosphytylation reaction was performed as described in Oskolkova O V et al. (Chem. Phys. Lipids 1999, 99 (1): 73-86). The product (3) was isolated with 84.8% yield. Rf (hexane-ethyl acetate-triethylamine, 10:4:0.5 v/v/v): 0.86.

Example 4: Synthesis of 1-O-Hexadecyl-2-deoxy-2-(tert-butoxycarbonyl)amino-sn-glycero-phosphocholine (6)

The reaction between phosphoramidite (3) and choline tosylate (Sigma-Aldrich) was performed in the presence of tetrazole as described in Oskolkova O V et al. (Chem. Phys. Lipids 1999, 99(1):73-86). The product (4) was afterwards oxidized from phosphorus-III to phosphorus-V in the presence of tert-butyl hydroperoxide. The cyanoethyl protective group was removed by action of TEA. These reactions were performed as one-pot reactions as described in Oskolkova O V et al. (Chem. Phys. Lipids 1999, 99 (1):73-86). The product (6) was purified on a DSC-C18 column (500 mg, 3 ml, Sigma-Aldrich) using a gradient of MeOH in water (from 50% MeOH to 100% MeOH). After evaporation of solvents from fractions containing the product (6), it was obtained with 63.3% yield. Rf (system B): 0.36.

Example 5: 1-O-Hexadecyl-2-deoxy-2-amino-sn-glycero-phosphocholine (7)

The phosphate (6) (49.8 mg, 85.7 µmol) was dissolved in 2 ml of dichloromethane and trifluoroacetic acid (1.5 ml, 19.6 mmol) was added. After 1.5 hr at room temperature the reaction was complete as detected by TLC. The mixture was evaporated under vacuum and co-evaporated several times with toluene. The product was further used without additional purification. The amount of the product was determined by the phosphorus assay. Rf (system B): 0.21. 1H-NMR (400 MHz, CDCl3: CD3OD, 2:1, v/v) (δ, ppm): 0.88 (t, 3H, CH3 (1)), 1.22-1.38 (m, 24H, (CH2)12 (2-13)), 1.37 (m, 2H, CH2 (14)), 1.5-1.62 (m, 2H, CH2 (15)), 3.36 (s, 9H, (CH3)3 (γ), 3.58 (m, 1H (β1)), 3.72-3.81 (m, 4H, (2-CH2) (ω1, β)), 3.9 (d, 2H, CH2 (ω1)), 4.24 (d, 4H, CH2 (α, ω2)).

Calculated for $C_{24}H_{53}N_2O_5P$: 480.36 g/mol; found m/z: 481.5 [M+H]$^+$.

Example 6: 1-O-Hexadecyl-2-deoxy-2-(prostaglandin E2)amino-sn-glycero-3-phosphocholine (KFU-PGE2)

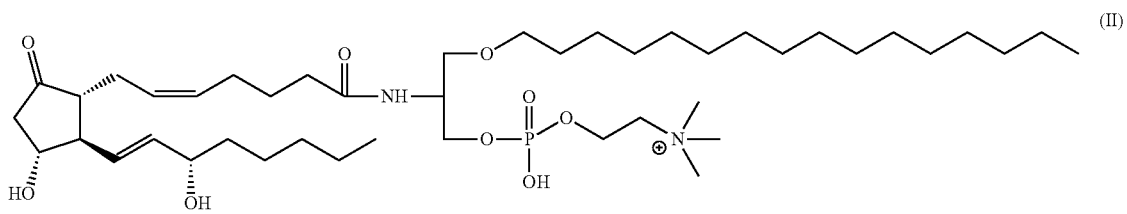 [SMILES: CCCCCCCCCCCCCCCCOCC(COP(=O)(O)OCC[N+](C)(C)C)NC(=O)CCC/C=C\C[C@H]1C(=O)C[C@@H](O)[C@@H]1/C=C/[C@@H](O)CCCCC]

(II)

In a glass vial with PGE2 (1 mg, 2.95 µmol) dissolved in 100 µl methyl acetate, EDC (1 mg, 5.22 µmol) and N-hydroxysuccinimide (0.44 mg, 3.80 µmol) and 1 ml dichloromethane were added. The reaction mixture was overlaid with argon and kept at room temperature for 18 hrs. TLC control (system A) showed the reaction was complete. The product was extracted according to the method analogous to Folch method: methanol (0.5 ml) was added, mixed well, then water (0.375 ml) was added and vortexed. The lower phase was transferred into a fresh glass vial, the solvents were evaporated under a stream of argon. Afterwards, 2-amino-2-deoxy-1-O-hexadecyl-sn-glycero-phosphocholine (7) (1.44 mg, 3 µmol) and THF (1 ml) and 10 µl TEA were added. The reaction mixture was flushed with argon and kept at room temperature on a shaker for 18 hrs. The mixture was evaporated under a stream of argon. The product was purified on SPE-C18 cartridge using a gradient of 50 to 100% methanol in water with addition of 0.2 vol-% of formic acid. The fractions containing pure product were evaporated under a stream of argon. Rf (system B): 0.28.

Calculated for $C_{44}H_{83}O_9N_2P$: 814 g/mol; found m/z: 815.7 [M+H]$^+$.

Example 7: 1-O-Hexadecyl-2-deoxy-2-(8-iso-prostaglandin E2)amino-sn-glycero-3-phosphocholine (KFU-iPGE2)

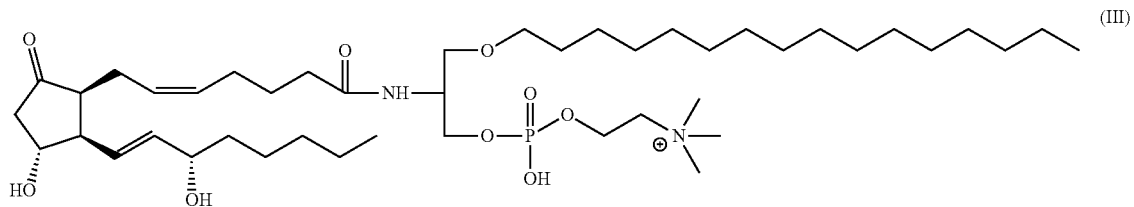 [SMILES: CCCCCCCCCCCCCCCCOCC(COP(=O)(O)OCC[N+](C)(C)C)NC(=O)CCC/C=C\C[C@@H]1C(=O)C[C@@H](O)[C@@H]1/C=C/[C@@H](O)CCCCC]
(III)

This compound was prepared as described in Example 6. Rf (system B): 0.28.
Calculated for $C_{44}H_{83}O_9N_2P$: 814.6 g/mol; found m/z: 815.7 $[M+H]^+$, 837.8 $[M+Na]^-$.

Example 8: 1-O-Hexadecyl-2-deoxy-2-(iloprost)amino-sn-glycero-3-phosphocholine (ILO-PC, KFU-ILO)

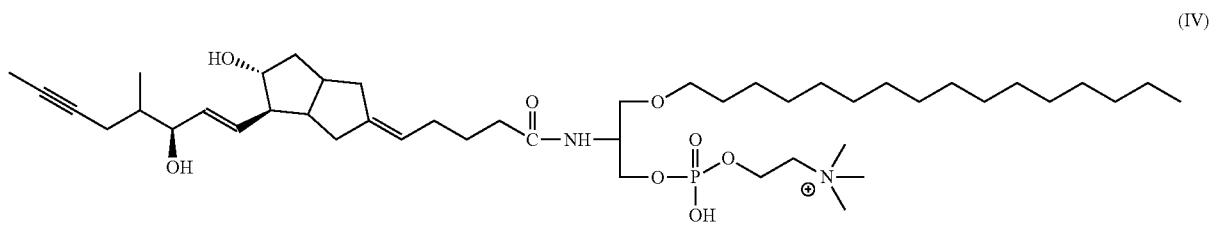 [SMILES: CC#CCC(C)[C@H](O)/C=C/[C@@H]1C2C/C(=C/CCCC(=O)NC(COCCCCCCCCCCCCCCCC)COP(=O)(O)OCC[N+](C)(C)C)CC2C[C@H]1O]
(IV)

The synthesis was performed as described in Example 6. Purification of the synthesized ILO-NH-PC was achieved on an SPE cartridge (SupelClean LC-18, 50 mg, 1 ml, Sigma-Aldrich) using a gradient of ethanol in water from 40% to 100%. Rf (system B): 0.38. Calculated for $C_{46}H_{83}N_2O_8P$: 822.6 g/mol; found m/z 823.67 $[M+H]^+$, 845.67 $[M+Na]^+$.

Example 9: 1-O-Hexadecyl-2-deoxy-2-(prostaglandin $F_{2\alpha}$)amino-sn-glycero-3-phosphocholine (KFU-PGF$_{2\alpha}$)

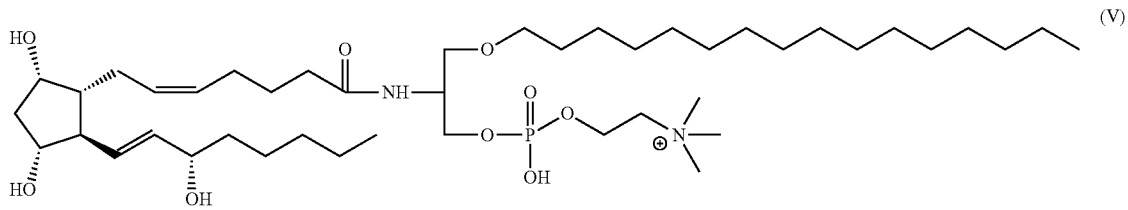 [SMILES: CCCCCCCCCCCCCCCCOCC(COP(=O)(O)OCC[N+](C)(C)C)NC(=O)CCC/C=C\C[C@@H]1[C@@H](/C=C/[C@@H](O)CCCCC)[C@H](O)C[C@@H]1O]
(V)

The compound was prepared from prostaglandin F2α as described in Example 6. Rf (system B): 0.25. Calculated for $C_{44}H_{85}N_2O_9P$: 816.6 g/mol; found m/z 817.83 $[M+H]^+$, 839.83 $[M+Na]^+$.-

Example 11: 1-O-Hexadecyl-2-deoxy-2-(12-hydrpxydpdecanyl)amino-sn-glycero-3-phosphocholinelin (KFU-12-(OH)-C12)

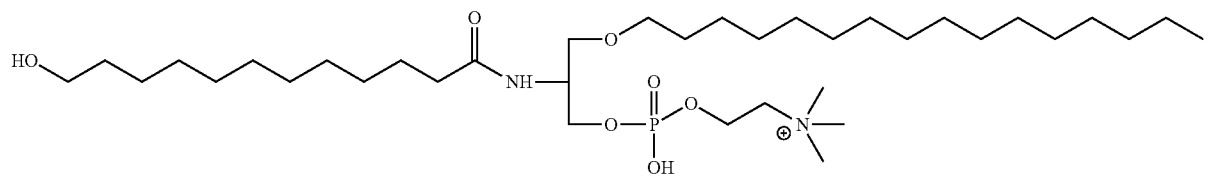

(VI)

The synthesis was performed as described in Example 6 starting from 12-hydroxydodecanoic acid. The product 12(OH)—C12-PC was isolated using SupelClean LC-18 SPE cartridges (50 mg, 1 ml) and a gradient of MeOH from 50% to 100% in water.Rf (system B): 0.24. Calculated for $C_{36}H_{75}N_2O_7P$: 678.5 g/mol; found: $[M+H]^+$ 679.58, $[M+Na]^+$ 701.67.

Example 11: 1-O-Hexadecyl-2-deoxy-2-(8-iso-prostaglandin $A_2$)amino-sn-glycero-3-phosphocholine (KFU-iPGA2)

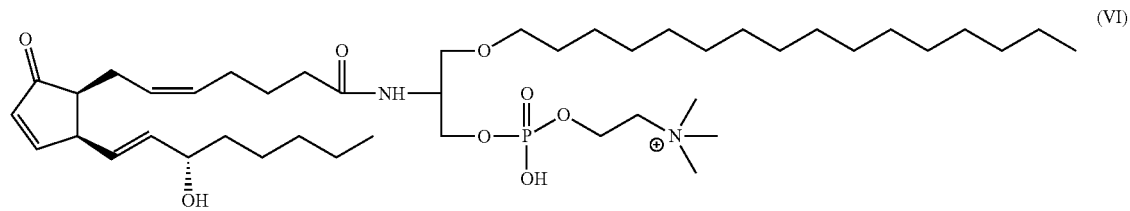 [SMILES: CCCCCCCCCCCCCCCCOCC(COP(=O)(O)OCC[N+](C)(C)C)NC(=O)CCC/C=C\C[C@@H]1C(=O)C=C[C@@H]1/C=C/[C@@H](O)CCCCC]

(VI)

The synthesis was performed as described in Example 6 starting from 1 mg of 8-iso-prostaglandin A2. Calculated for $C_{44}H_{81}N_2O_8P$: 796 g/mol; found 797.54 $[M+H]^+$, 819.54 $[M+Na]^+$.

Example 12: Anti-LPS and Barrier-Protective Biological Effects of Compounds Comprising 1-O-hexadecyl-2-deoxy-2-amino-sn-glycero-phosphocholine (7) as a Scaffold Material and Methods:

Human ECs were preincubated with different concentrations of phospholipids (PLs) in M199/2% FCS for 15 min followed by addition of LPS (serotype 055: B5, 30 ng/ml final concentration; Sigma-Aldrich). The cells were incubated at 37° C. and 5% CO2 for 4 to 6 hrs. Cell culture supernatants were collected and analyzed by IL-8 ELISA. Measurement of E-Selectin exposed on the cell surface was proceeding as described by Bochkov et al. (Nature, 2002, 419(6902):77-81).

Measurements of Endothelial Monolayer Permeability

The cellular barrier properties were analyzed by measurements of transendothelial electrical resistance (TER) across confluent human pulmonary artery endothelial monolayers using an electrical cell-substrate impedance sensing system (Applied Biophysics, USA) as previously described (Birukova A A et al., Am. J. Physiol. Lung Cell. Mol. Physiol. 2006, 290(3):L540-548; Birukova A A et al. FASEB J. 2004, 18(15):1879-1890).

Animal Studies.

All animal care and treatment procedures were approved either by the University of Chicago Institutional Animal Care and Use Committee or by University of Graz.

Treatment of Mice With PGE2-KFU and LPS.

Experiments were performed according to Austrian animal rights law using female C57BL/6J mice (Jackson Laboratories, Germany) of 20 g body weight. Mice were injected i.p. with 200 µl of either with saline, phospholipid (200 µg/mouse), LPS (*Escherichia coli* O55:B5, 20 µg/mouse) or a combination of LPS and the phospholipid. After 2 and 4 hrs blood was taken retroorbitaly and placed into Eppendorf tubes containing EDTA. After centrifugation of cells, plasma was collected and analyzed by ELISA for murine KC.

Treatment of Mice With ILO vs ILO-PC.

Eight-week old C57B1 mice were purchased from Jackson Laboratories (Bar Harbor, USA). Animals were handled according to the National Institutes of Health Guide for the Care and Use of Laboratory Animals. Bacterial lipopolysaccharide (LPS, 0.63 mg/kg body wt; *Escherichia coli* O55: B5) or sterile water was injected intratracheally in a small volume (20-30 µl) using a 20-gauge catheter (Exelint International, USA). Iloprost (10 µg/kg), ILO-PC (10 µg/kg) or sterile saline solution was administrated concurrently and 5 hrs after LPS instillation by intravenous injection in the external jugular vein. Animals were sacrificed at day-1 or day-3 by exsanguination under anesthesia. BAL was performed using 1 ml of sterile Hanks balanced salt buffer and measurements of cell count and protein concentration were conducted as previously described (Fu P et al., Eur. Respir. J. 2009, 33:612-624). For analysis of LPS-induced lung vascular leak, Evans blue dye (30 ml/kg) was injected into the external jugular vein 2 hrs before termination of the experiment.

In vivo optical imaging: Mice were injected with 100 µl of 2 nmol Angiosense 680 EX (a vascular fluorescent blood pool imaging agent purchased from PerkinElmer, USA), intravenously via tail vein. Fluorescence optical imaging was performed in the Integrated Small Animal Imaging Research Resource (iSAIRR) at the University of Chicago using Xenogen IVIS 200 Spectrum (Caliper Life Sciences, USA). Mice were exposed to isoflurane anesthesia with $O_2$ through the gas anesthesia manifold and placed on the imaging stage. Acquisition and image analysis were performed with Living Image 4.3.1 Software.

Statistical analysis. Results are expressed as means±SD of three to five independent experiments. Stimulated samples were compared with controls by unpaired Student's t-test. $P<0.05$ was considered statistically significant.

Figure 2:
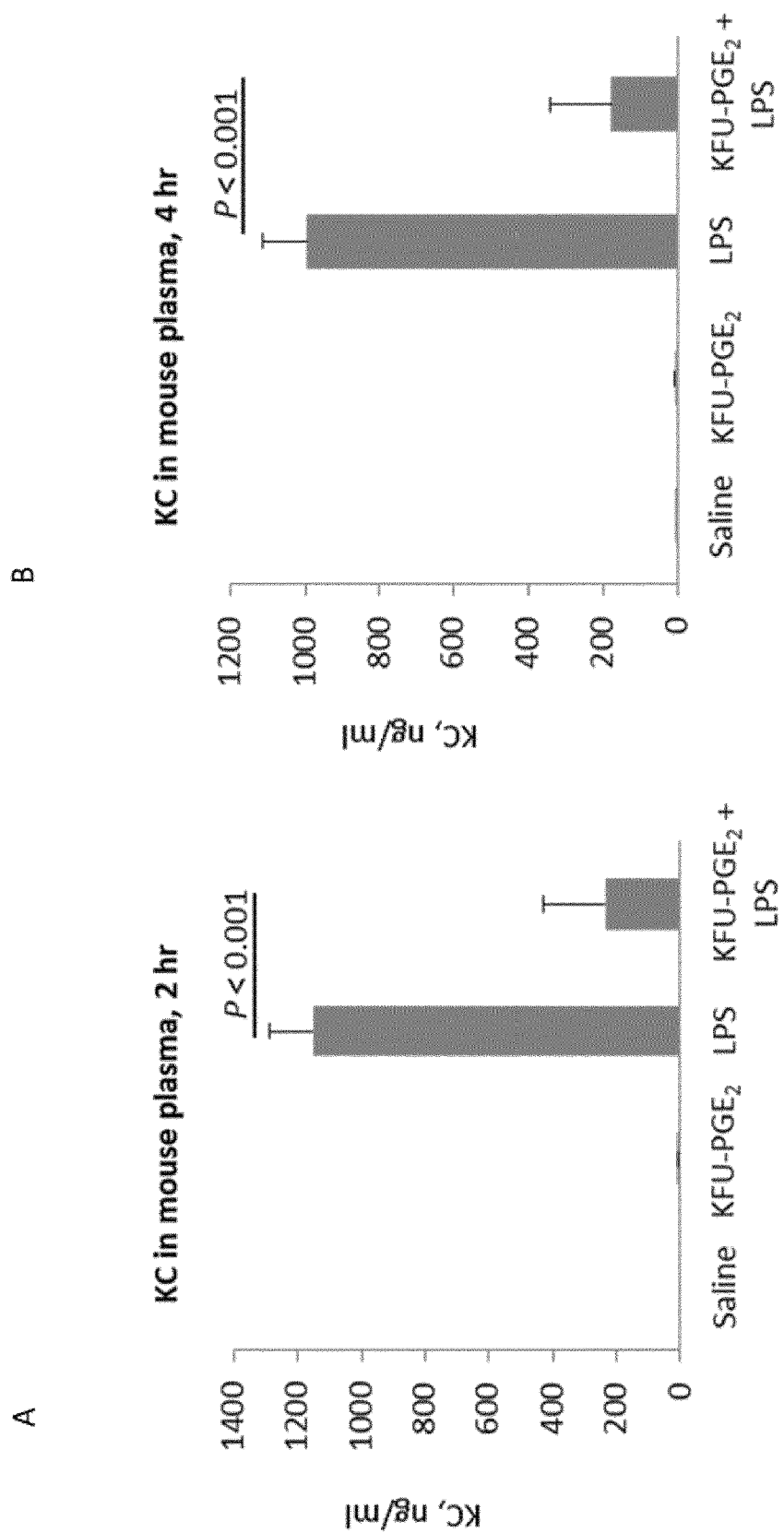
FIG. 2 shows that KFU-PGE2 i.e. compound (II) of example 6 inhibits induction of inflammatory chemokine KC in mice injected with LPS. Mice were injected i.p. with 200 µl of either with saline, phospholipid (200 µg/mouse), LPS (20 µg/mouse) or a combination of LPS and phospholipid. After 2 and 4 hrs blood was taken. After centrifugation of cells, plasma was collected and analyzed by ELISA for murine chemokine KC.

Results:

As a starting point for development of a lead structure prostaglandin E2, isoprostaglandin E2 and isoprostaglandin A2 were attached to the KFU-scaffold. Similarly to natural PAPC (1-palmitoyl-2-arachidonoyl-sn-glycero-3-phosphocholine, PAPC) oxidized in the presence of air for 24 hours (Bochkov V N et al., Nature 2002; 419(6902):77-81; Oskolkova O V et al., J. Immunol. 2010, 185(12):7706-12), prostanoids linked to compound (7) inhibited activation of Toll-like receptors (FIG. 1) and protected animals from LPS-induced inflammation in vivo (FIG. 2).

Figure 3:
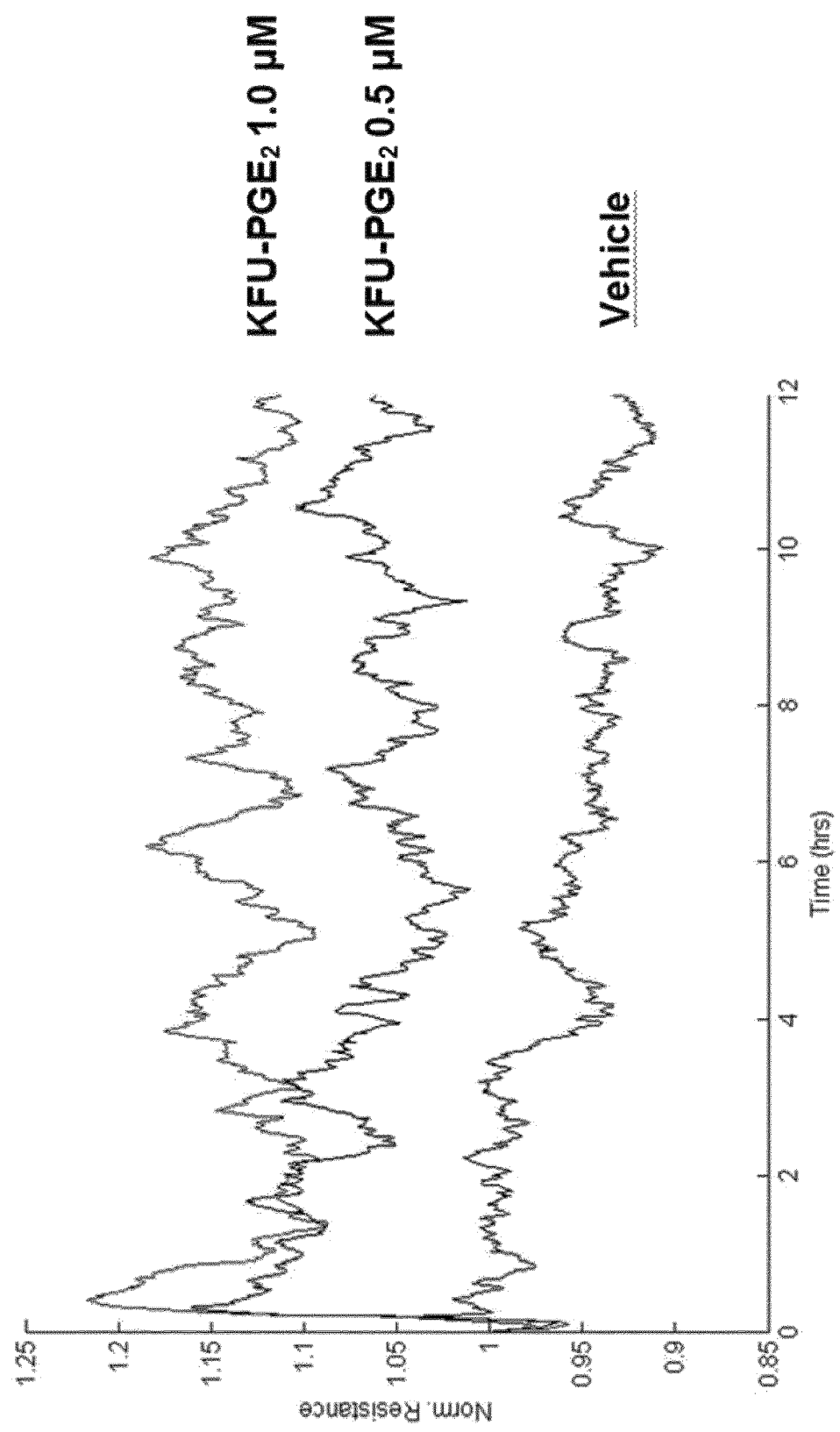
FIG. 3 shows that KFU-PGE2 protects endothelial cell barrier. Analysis of the endothelial barrier was performed as described in example 13. The cells were stimulated with two concentrations of KFU-PGE2.

Apart from inhibiting the LPS-induced inflammation, the prostanoids bound to compound (7), similarly to natural oxidized PAPC (Birukov K G et al., Circ. Res. 2004, 95(9)892-901), were able to enhance the endothelial barrier in cultured endothelial cells (see FIG. 3).

Figure 4:
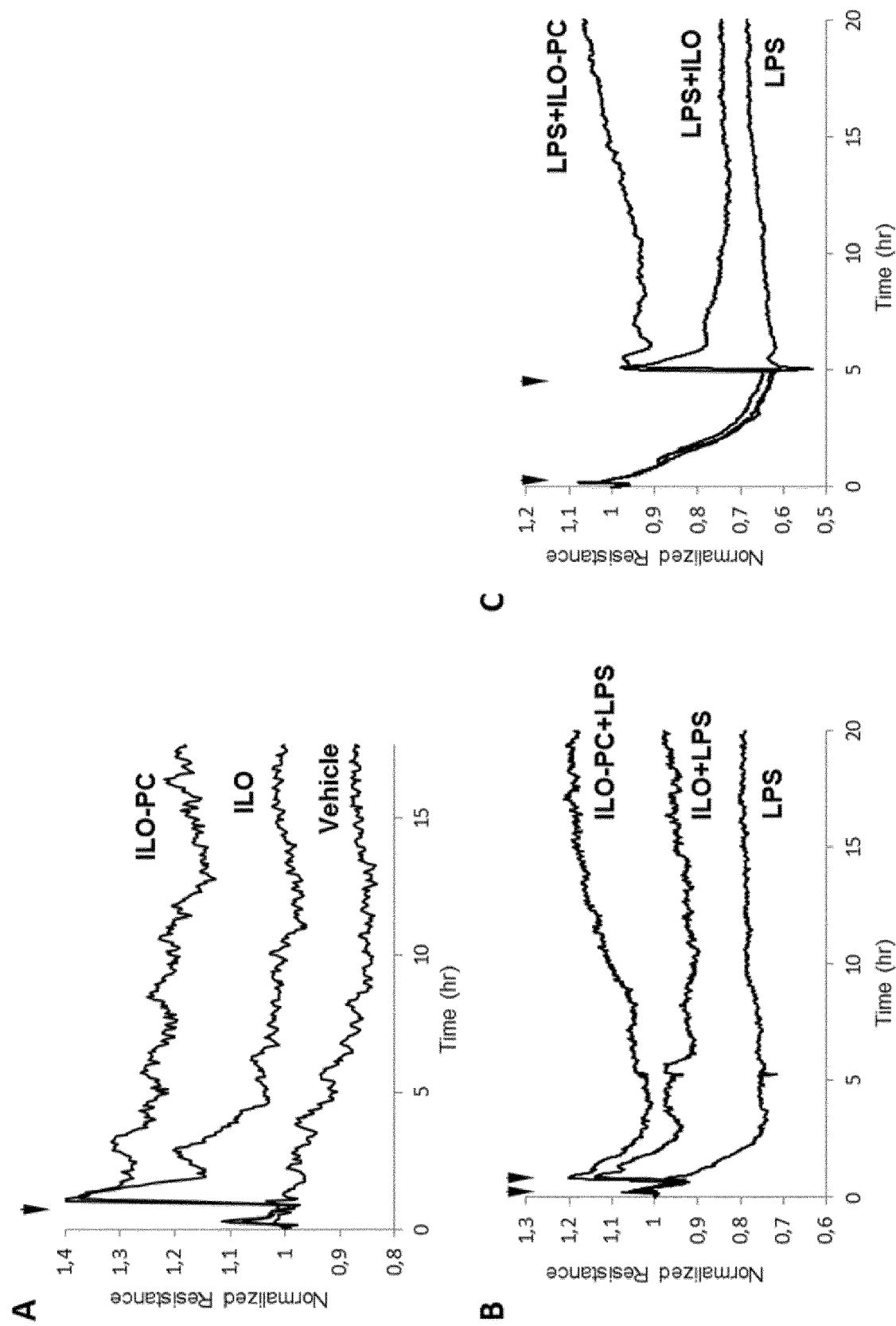
FIG. 4 shows that KFU-iloprost (ILO-PC) induces stronger endothelial barrier-protective effect than free Iloprost (ILO). A: Comparison of duration of EC barrier enhancement caused by ILO and ILO-PC (0.5 µM). Agonist-induced EC barrier-enhancing response was evaluated by TER measurements. B-C: Effect of ILO and ILO-PC (KFU-ILO) post-treatment on EC permeability induced by LPS (200 ng/ml). At the time indicated by the first arrow, pulmonary EC plated on microelectrodes were stimulated with LPS. At the time indicated by the second arrow, vehicle, ILO, or ILO-PC were added 15 min (B) or 5 hrs after LPS addition (C). Transendothelial resistance reflecting EC monolayer barrier properties was monitored over 20 hours.
Figure 5:
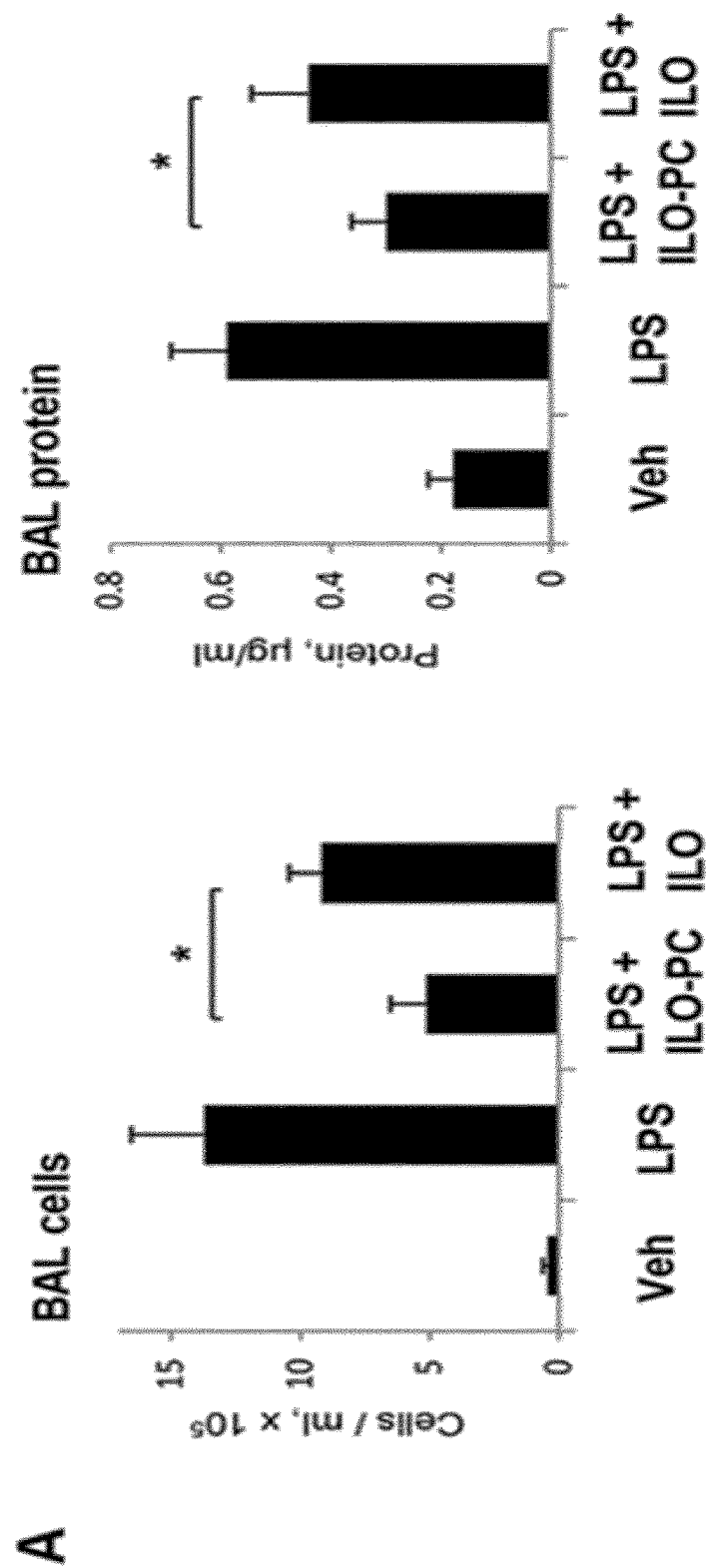
FIG. 5 shows that KFU-ILO (ILO-PC) induces better protective response on LPS-induced lung injury and barrier dysfunction compared to a free molecule. A: Analysis of protein concentration and total cell count was performed in BAL samples obtained from control and experimental groups after LPS (0.7 mg/kg, i.t.) challenge. B: The levels of TNFα were measured in BAL samples using ELISA assay. C: Live imaging analysis of lung vascular barrier dysfunction after LPS intratracheal injection with and without intravenous administration of ILO or ILO-PC (KFU-ILO). LPS-induced accumulation of fluorescent Angiosense 680 EX imaging agent in the lungs of same animals was detected by Xenogen IVIS 200 Spectrum imaging system 1 day and 3 days after LPS challenge.
Figure 5:
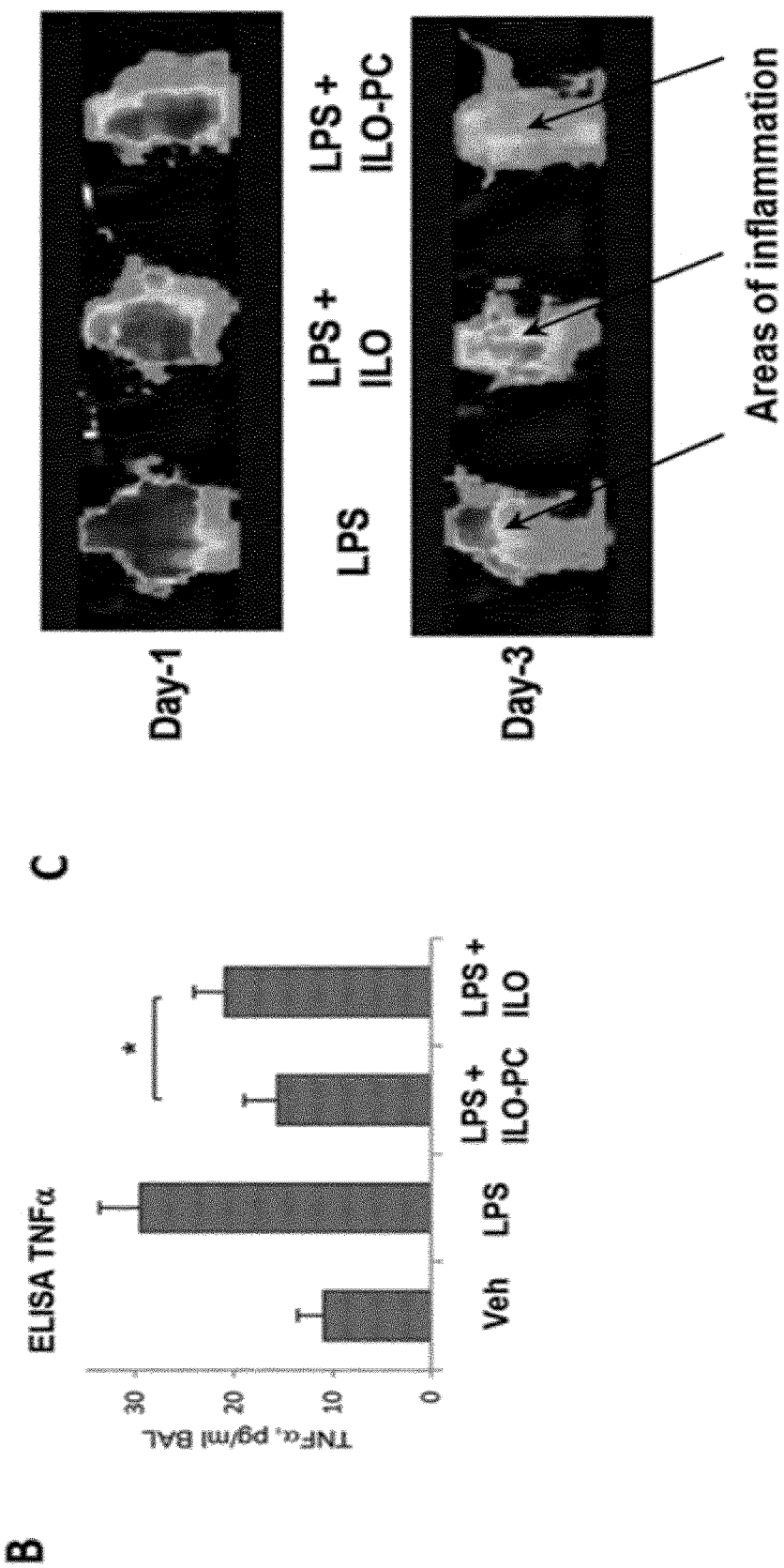

The phospholipid-like scaffold (compound (7)) was also used as a carrier for known barrier-protective oxidized lipids such as prostacyclin analogue iloprost ((5E)-5-[(3aS,4R,5R,6aS)-5-hydroxy-4-[(E,3S)-3-hydroxy-4-methyloct-1-en-6-ynyl]-3,3a,4,5,6,6a-hexahydro-1H-pentalen-2-ylidene]pentanoic acid). The KFU-conjugated iloprost demonstrated stronger and more prolonged barrier-protective activity as compared to free iloprost (FIG. 4). Furthermore, KFU-iloprost demonstrated better protection from edema in vivo as compared to free molecule of this drug (FIG. 5).

Conclusion:

In summary, the data clearly show that phospholipase-resistant analogues of oxidized phospholipids demonstrate similar or better anti-LPS and endothelial barrier-protective activities as compared to natural phospholipid scaffolds. Further advantage of the compounds of the present invention is increased biostability and simplicity of synthesis. In addition, the data show that compound (7) can be a carrier for other barrier-protective drug molecules thus enhancing their action and increasing duration of protective effect.

The synthetic compounds have been shown to inhibit inflammatory reactions caused by TLR2 agonists.

Additionally, the synthetic compounds prepared showed better pharmacodynamics and pharmacokinetics (for example increased stability) of the drugs included into the KFU-scaffold.

Example 13: Cell Survival Tests

Human ECs (HUVECs and HUVECtert) were cultured Nunclon™ Delta surface flasks (Bartelt; Graz, Austria) in the medium M199 (Gibco) supplemented with 20% fetal calf serum (FCS, Gibco; Carlsbad, Calif., USA), penicillin-streptomycin-amphotericin B (PSF, Lonza; Basel, Switzerland), glutamine (Lonza) and ECGS-heparin (PromoCell; Heidelberg, Germany) in the 95% humidified atmosphere with 5% $CO_2$ at 37° C. For stimulation of cells, they were seeded in the same medium in 96-well Nunclon™ Delta plates (Bartelt). On the day 2, the full medium was exchanged to M199 medium without serum but containing lipids (100 µl per well). In experiments on cell survival against hydrogen peroxide, camptothecin or doxorubicin, the full medium was exchanged to M199 containing 7% FCS and OxPAPC at 40 µg/ml or 50 µg/ml added as a two-fold concentrated solution (50 µl per well). After 20 to 30 min preincubation, toxic agents were added also as two-fold concentrated solutions in M199/7% FCS (50 µl per well). Final concentrations of lipids and toxic agents are indicated in figures. After 16 to 72 hrs of cell incubation at 37° C. and 5% $CO_2$ in 95% humidity, either a nuclei counting of the remained cells or an XTT assay were performed. For the nuclei counting, the medium containing dead cells was aspirated and a Hoechst 33342 solution at the concentration of 1 µg/ml in PBS containing $Ca^{2+}$ and $Mg^{2+}$ (50 µl per well) was added. After at least 20 min incubation of cells at 37° C. in the cell culture incubator, the stained nuclei were counted using the EnSight plate reader (Perkin-Elmer; Waltham, Mass., USA). An XTT assay with the incubation time of 2 hrs was performed as described (Oskolkova, Godschachner and Bochkov, Inflammation 2017; 40(2): 530-536).

Results and Discussion

It was found that in addition to their anti-inflammatory and anti-edemagenic action OxPLs induced general protective effects on endothelial cells. In other words, OxPLs protected endothelial cells from different types of cellular stress. Two readouts producing qualitatively similar results were used in order to assess the protective action, namely i) analysis of the metabolic activity of HUVECs and ii) counting cell nuclei stained by Hoechst 33342. The latter assay is an equivalent of counting live cells that are known to remain adherent to culture dish after treatment with toxins, while dead cells are washed away.

The experiments demonstrated that OxPLs such as OxPAPC or synthetic PLA2-resistant NH-OxPCs protected HUVECs from cell death induced by serum deprivation (1 May 2018; 23 Jun. 2018), oxidative stress (hydrogen peroxide, 11 Jun. 2018; 6 Apr. 2018) or toxic drugs such as camptothecin (13 Jun. 2018) or doxorubicin (31 Mar. 2018). In other words, OxPLs increased general resistance of endothelial cells to different types of stress.

Importantly, qualitatively similar protective effects were induced both by complex OxPL mixtures generated by nonenzymatic peroxidation of a single precursor, such as oxidized palmitoy-arachidonoyl-PC (OxPAPC), as well as by individual synthetic PLA2-resistant NH-OxPLs such as PGE2-NH-PC (1 May 2018), PGF2a-NH-PC (1 May 2018) and iPGA2-NH-PC (23 Jun. 2018). In contrast to NH-OxPLs, free oxidized fatty acids like oxidized arachidonic acid (11 Jul. 2017) or iPGA2 (23 Jun. 2018) were not active, which points to the importance of the phospholipid scaffold for the protective activity.

The data show that OxPLs are capable of enhancing general stress tolerance in endothelial cells. Endothelial damage by toxic, edemagenic and proinflammatory compounds is a characteristic of lung edema and therefore preventing these deleterious effects is very likely to prevent barrier dysfunction.

Figure 6:
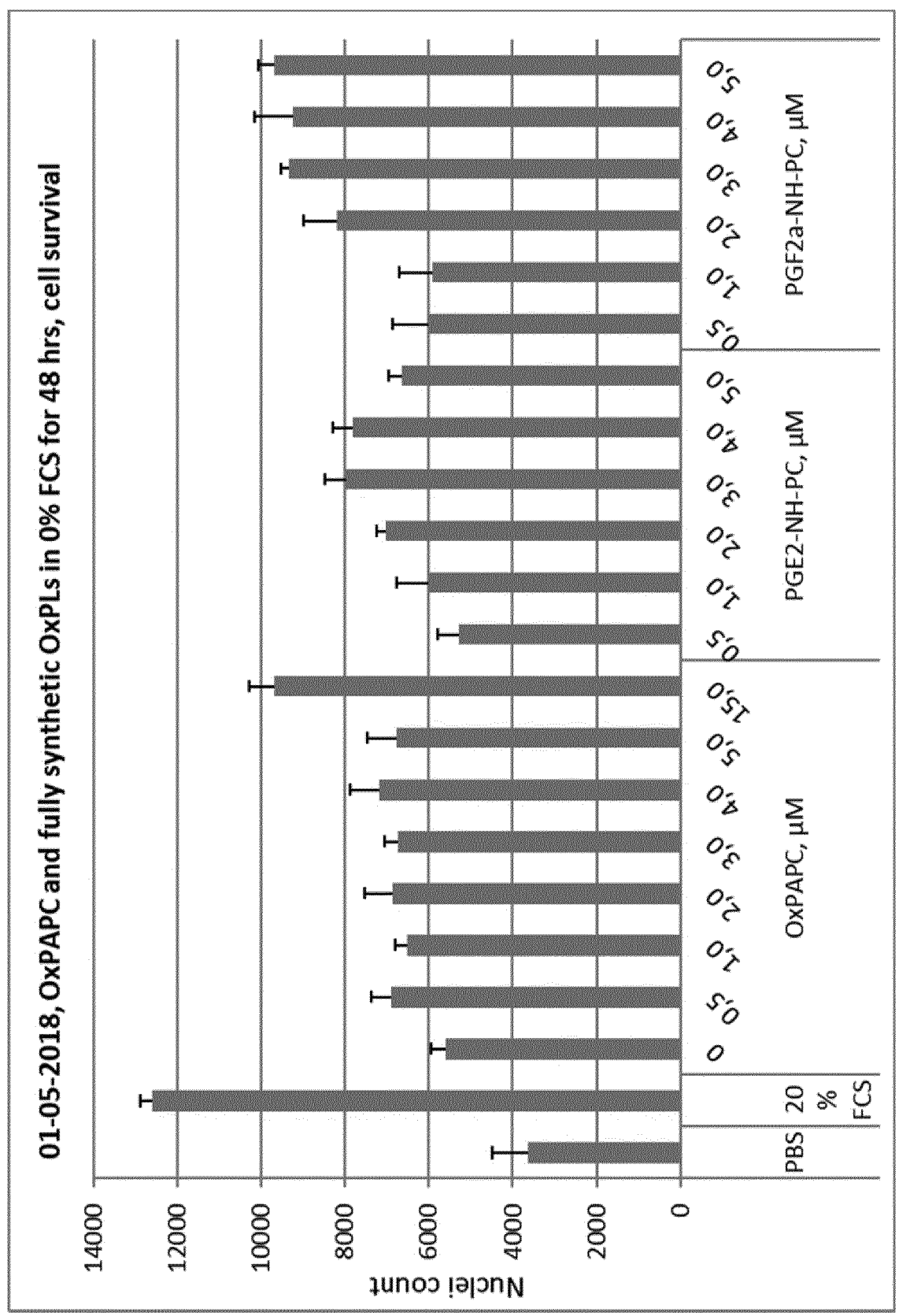
FIG. 6 shows that OxPLs protect endothelial cells (ECs) against serum deprivation.

A) OxPLs/Serum Deprivation (FIG. 6)

OxPLs protect endothelial cells (ECs) against serum deprivation. ECs were seeded in full M199 medium containing 20% serum. On the day 2, the medium was exchanged to M199 without serum and containing phospholipids at increasing concentrations. After 48 hrs, nuclei of remaining cells were stained by Hoechst and counted. Cells treated with 20% FCS serve as positive and with PBS as negative controls, respectively.

Figure 7:
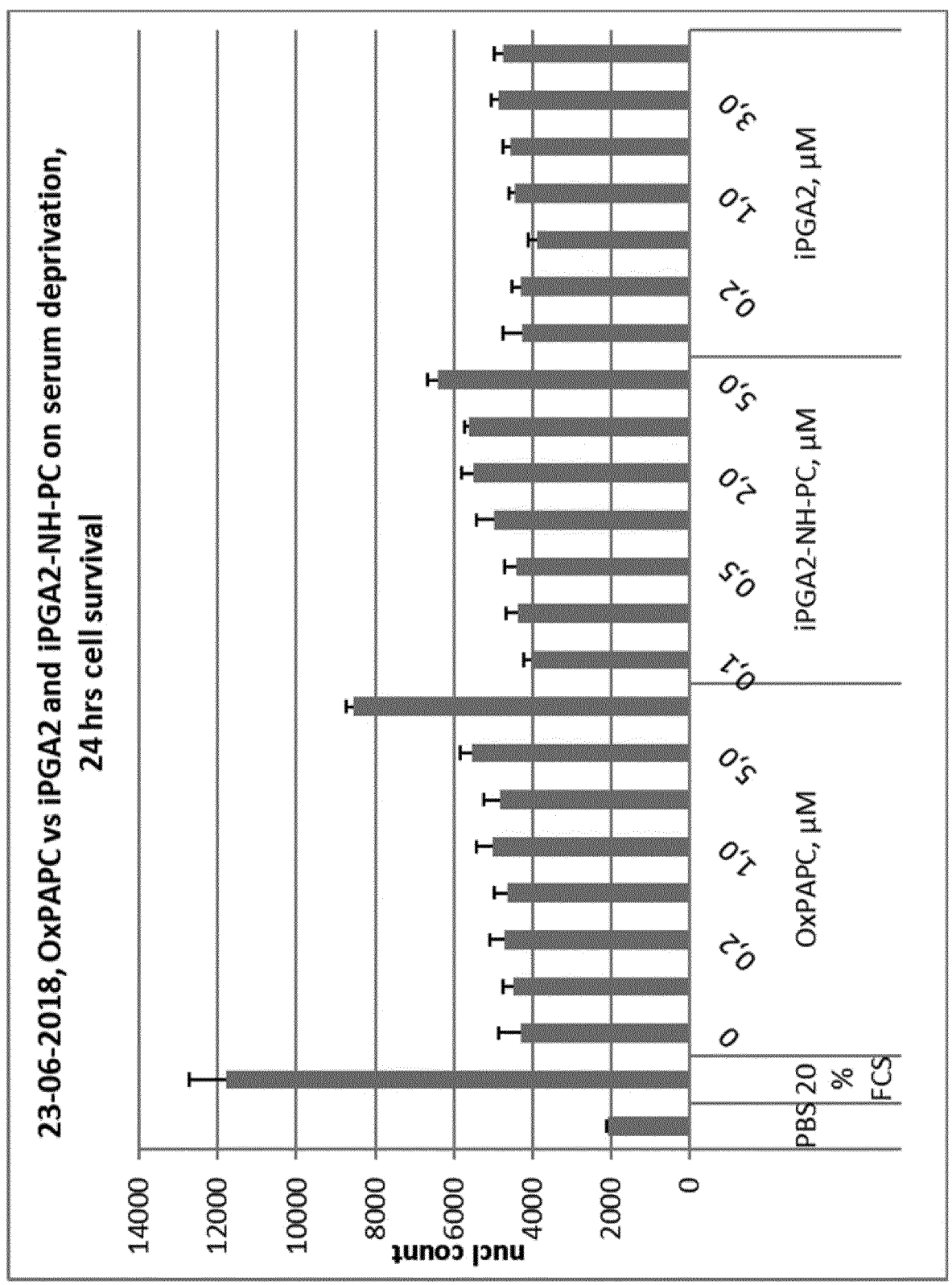
FIG. 7 shows that iPGA2-NH-PC and OxPAPC protect ECs against serum deprivation and that the effect depends on the phospholipid scaffold.

B) iPGA2-NH-PC and OxPAPC/Serum Deprivation (FIG. 7)

Fully synthetic iPGA2-NH-PC and OxPAPC protect ECs against serum deprivation and the effect depends on the phospholipid scaffold. ECs were treated as described in Example 13. After 24 hrs, nuclei of remaining cells were stained by Hoechst 33342 and counted. Cells treated with OxPAPC and 20% FCS serve as positive and with PBS as negative controls, respectively. It is to note that free, non-phospholipid bound iPGA2 was not protective.

Figure 8:
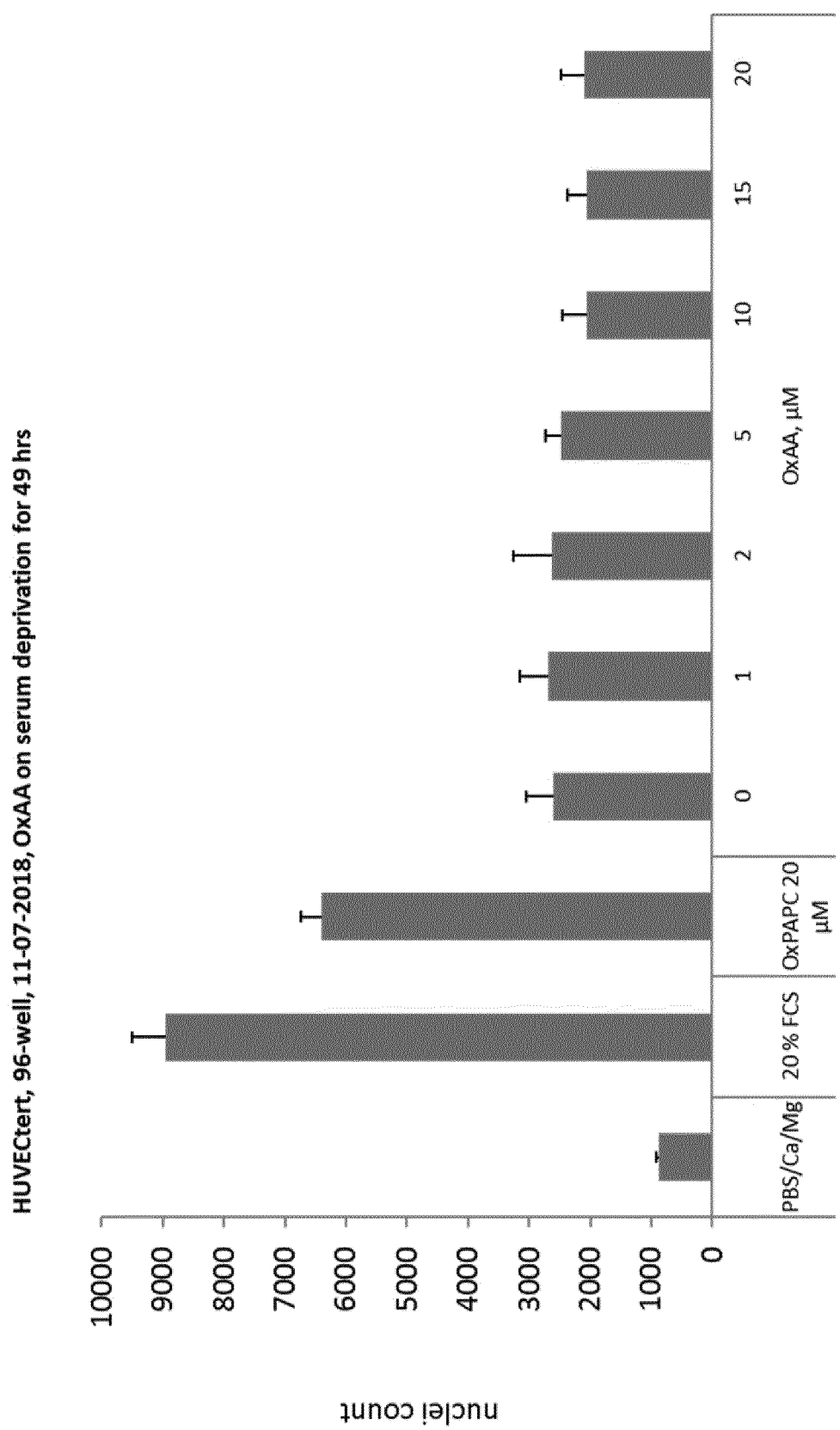
FIG. 8 shows that oxidized arachidonic acid (OxAA) is not active against serum deprivation.

C) Oxidized Arachidonic Acid (OxAA)/Serum Deprivation (FIG. 8)

Oxidized arachidonic acid (OxAA) is not active against serum deprivation. ECs were treated with increasing concentrations of OxAA as described in Example 13. After 49 hrs, nuclei of remaining cells were stained by Hoechst 33342 and counted. Cells treated with 20% FCS or with 20 μM OxPAPC serve as positive and with PBS as negative controls, respectively.

Figure 9:
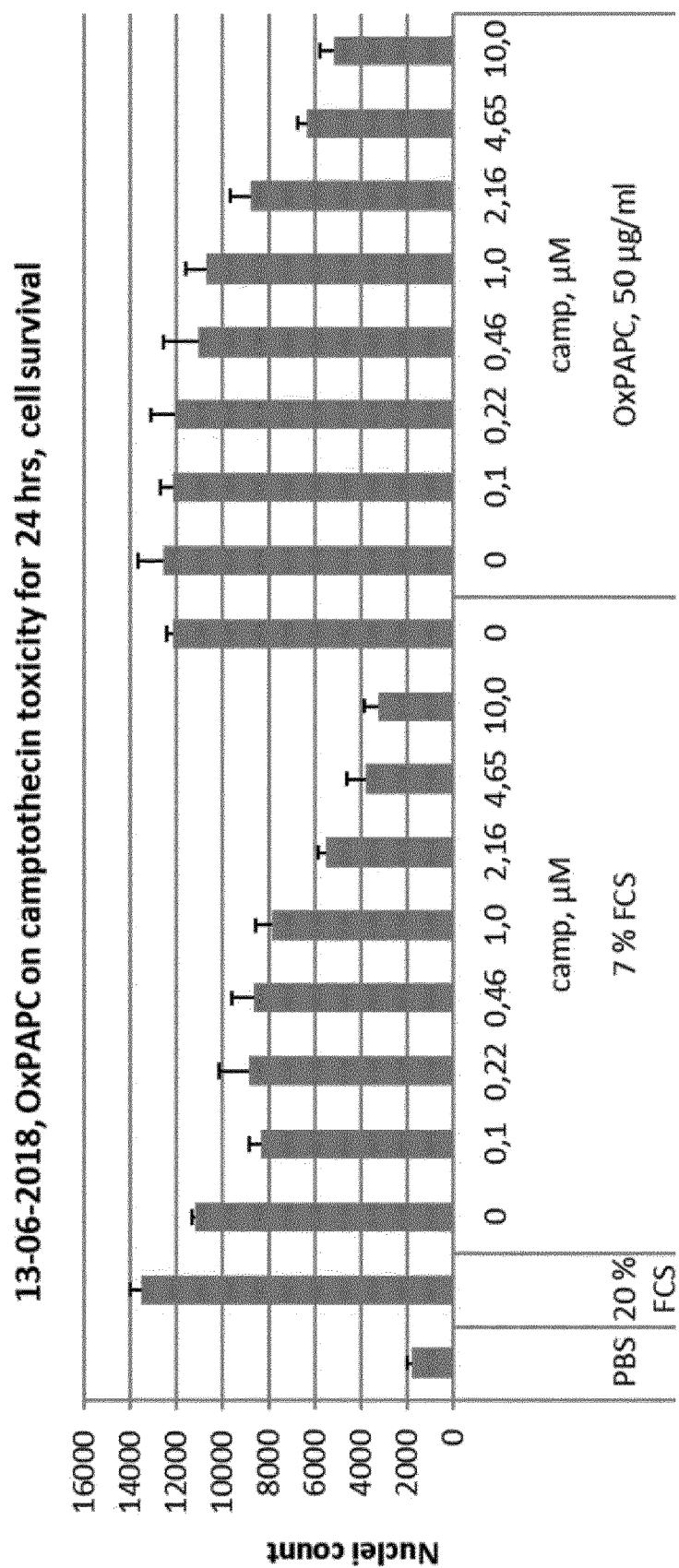
FIG. 9 shows that OxPLs protect ECs against toxicity caused by camptothecin.

D) Toxicity Caused by Camptothecin (FIG. 9)

OxPLs protect ECs against toxicity caused by camptothecin. ECs were seeded in full M199 medium containing 20% serum. On the day 2, the medium was exchanged to M199 with 7% serum and containing OxPAPC at 50 μg/ml. After 24 hrs in the cell culture incubator, nuclei of remaining cells were stained by Hoechst and counted. Cells treated with 20% FCS serve as positive and with PBS as negative controls, respectively.

Figure 10:
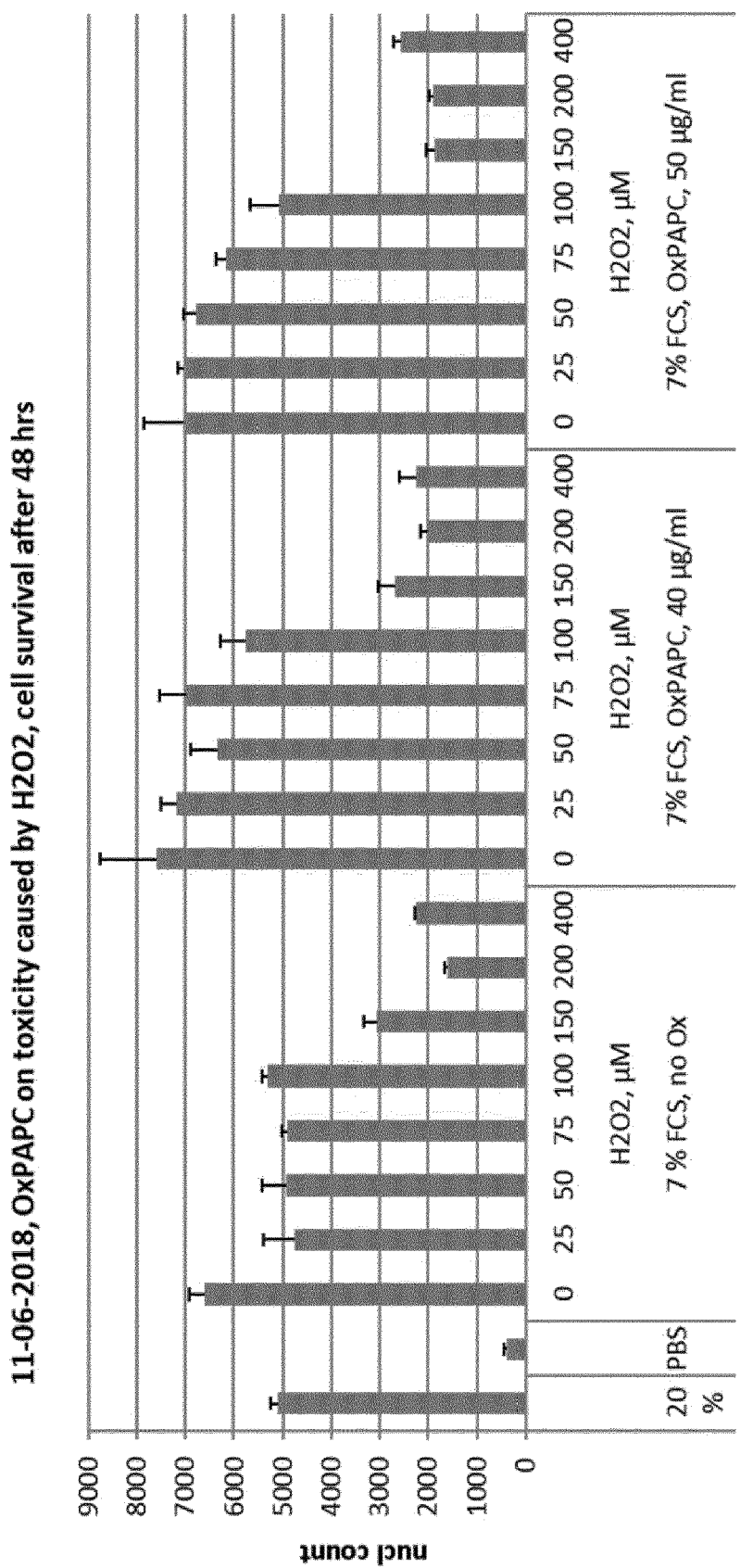
FIG. 10 shows that OxPLs protect ECs against toxicity caused by hydrogen peroxide ($H_2O_2$).

E) Toxicity Caused by Hydrogen Peroxide ($H_2O_2$) (FIG. 10)

OxPLs protect ECs against toxicity caused by hydrogen peroxide ($H_2O_2$). ECs were seeded in full M199 medium containing 20% serum. On the day 2, the medium was exchanged to M199 with 7% serum and containing OxPAPC at 40 or 50 μg/ml and increasing concentrations of H2O2. After 48 hrs, nuclei of remaining cells were stained by Hoechst 33342 and counted. Cells treated with 20% FCS serve as positive and with PBS as negative controls, respectively.

Figure 11:
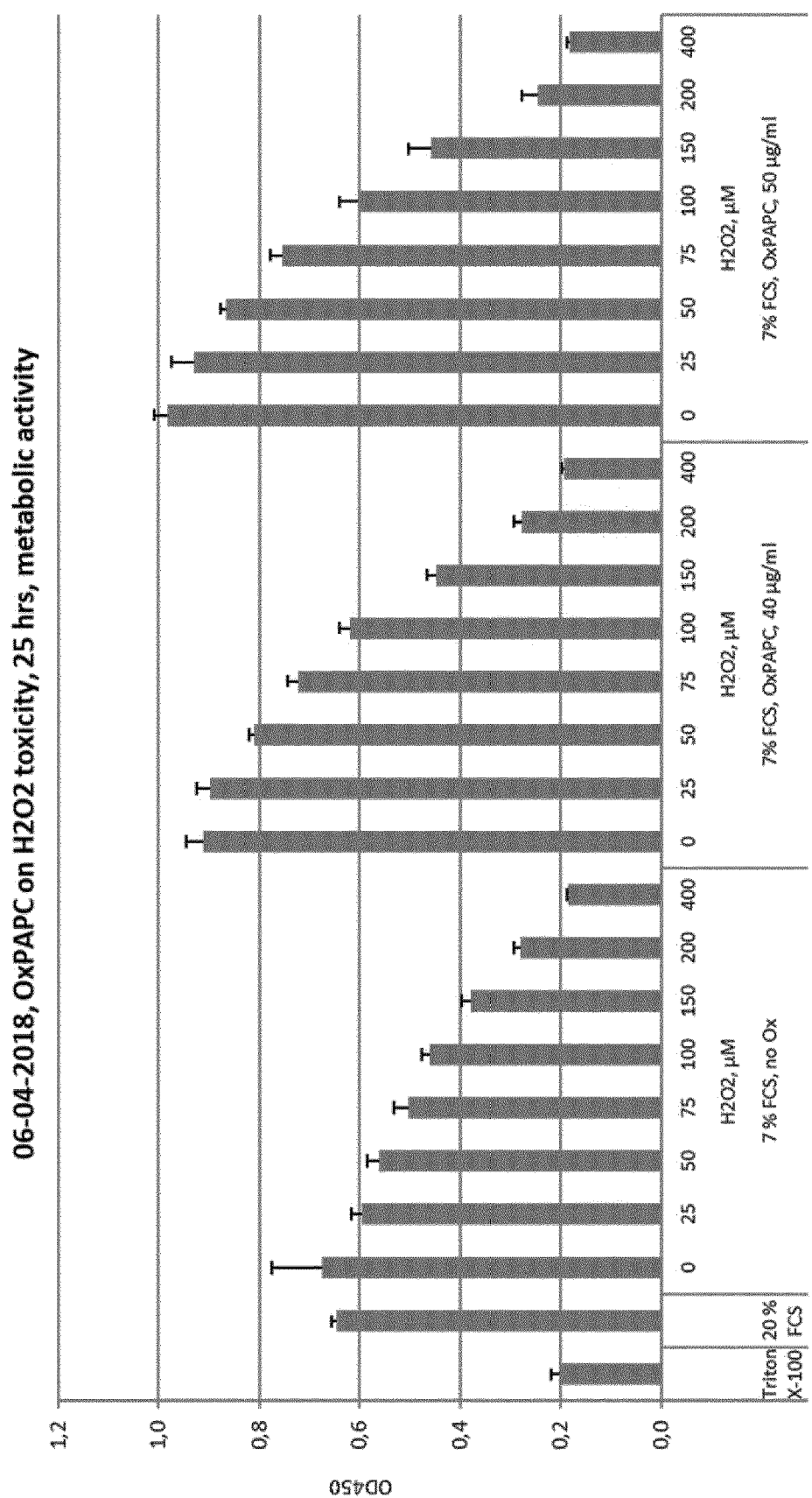
FIG. 11 shows also that OxPLs protect ECs against toxicity caused by hydrogen peroxide ($H_2O_2$).

F) Toxicity Caused by Hydrogen Peroxide ($H_2O_2$) (FIG. 11)

OxPLs protect ECs against toxicity caused by hydrogen peroxide ($H_2O_2$). ECs were treated as described under E). After 25 hrs, metabolic activity was measured by an XTT assay. Cells treated with 20% FCS serve as a positive control. Cells treated with 0.02% Triton X-100 represent dead cells.

Figure 12:
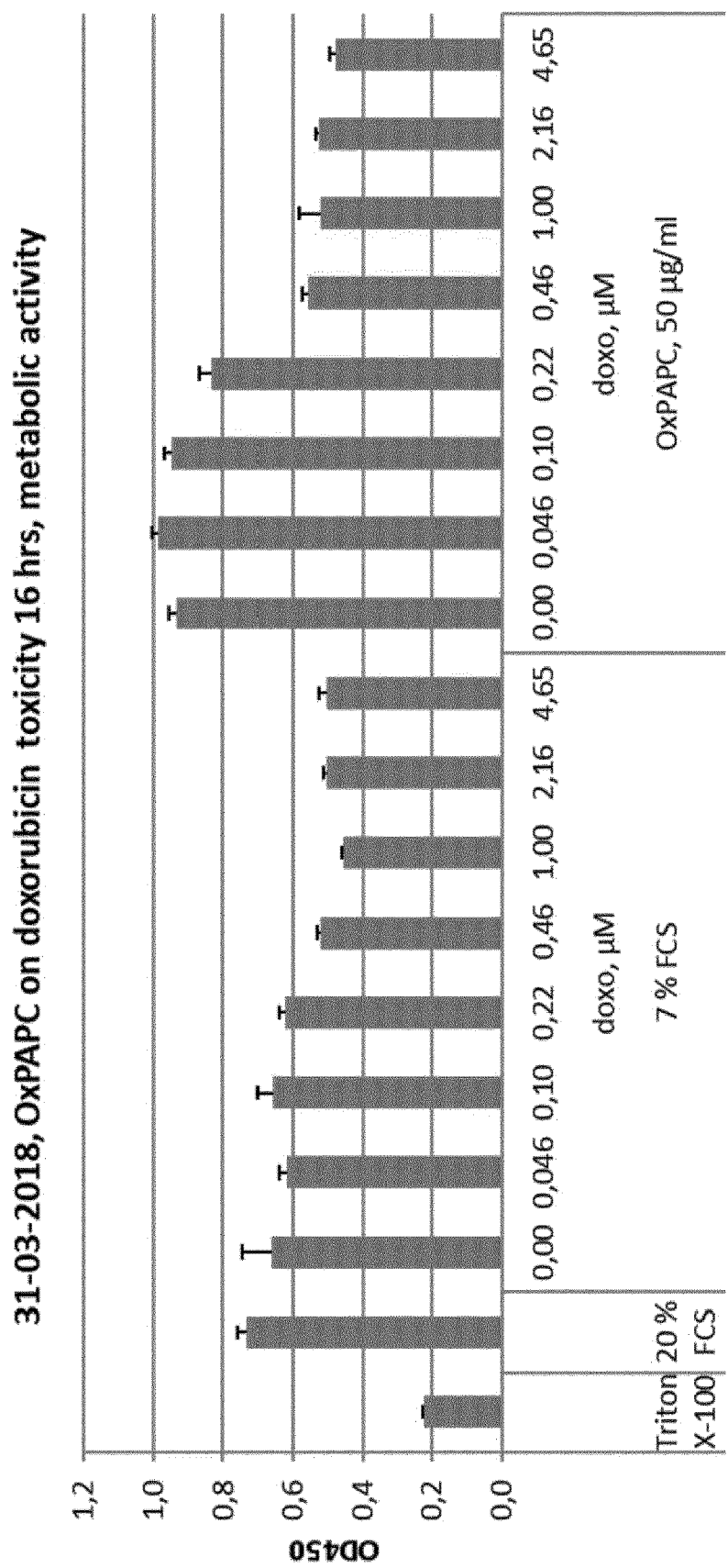
FIG. 12 shows that OxPLs protect ECs against toxicity caused by doxorubicin.

G) Toxicity Caused by Doxorubicin (FIG. 12)

OxPLs protect ECs against toxicity caused by doxorubicin. ECs were seeded in full M199 medium containing 20% serum. On the day 2, the medium was exchanged to M199 with 7% serum and containing OxPAPC at 50 μg/ml and increasing concentrations of doxorubicin. After 22 hrs, metabolic activity was measured by an XTT assay. Cells treated with 20% FCS serve as a positive control. Cells treated with 0.02% Triton X-100 represent dead cells.

The invention claimed is:

1. A compound having a structure according to formula (I)

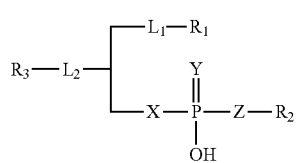

or a salt thereof, wherein $R_1$ is a branched or linear alkyl, acyl, alkenyl, hydroxyalkyl, hydroxyalkenyl, or hydroxy-alkinyl residue comprising 6 to 30 carbon atoms, $R_2$ is selected from the group consisting of
a) an alkyl residue comprising 1 to 10 carbon atoms and comprising a terminal or cyclic quaternary ammonium,
b) an alkyl residue comprising 1 to 10 carbon atoms and comprising a terminal amino group and/or 1 to 3 hydroxyl groups,
c) an amino acid residue,
d) a five or six carbon sugar and
e) H, $R_3$ is a residue selected from the group consisting of an alkyl, alkenyl, prostanyl-dialkyl, furanyl-dialkyl, cyclobutyl-dialkyl, cycloalkyl and aryl group of 2 to 40 carbon atoms length and comprising at least one keto group, epoxy group, aldehyde group, peroxy group, hydroperoxy group, hydroxyl group or a free carboxyl group, L1 is O, L2 is an amide group, X and Z are independently O, S or $CH_2$, and Y is selected from the group consisting of O and S.

2. The compound according to claim 1, wherein $R_1$ is a residue selected from the group consisting of hexyl residue, heptyl residue, octyl residue, nonyl residue, decyl residue, undecyl residue, dodecyl residue, tetradecyl residue, hexadecyl residue and octadecyl residue.

3. The compound according to claim 1, wherein $R_2$ is a choline residue.

4. The compound according to claim 1, wherein $R_2$ is inositol, glycerol, ethanolamine, serine or H.

5. The compound according to claim 1, wherein $R_3$ is an oxylipin selected from the group consisting of prostaglandins, isoprostanes, lipoxins, resolvins, protectins and maresins, monohydroxy-, dihydroxy-, trihydroxy-, tetrahydroxy fatty acid residues with epoxy-, keto-, hydroperoxy-, hydroxyl- or prostane groups independent of regio- and stereo-position of substituents within their structures.

6. The compound according to claim 1, wherein $R_3$ is selected from the group consisting of prostacyclins, prostaglandins, isoprostanes, lipoxins, maresins, resolvins and protectins.

7. The compound according to claim 1, wherein $R_3$ is a prostaglandin selected from the group consisting of prostaglandin E2, prostaglandin A2, prostaglandin F2α, prostaglandin B2, prostaglandin C2, prostaglandin D2, prostaglandin J2, 15-deoxy-Δ12,14-prostaglandin J2, deoxyprostaglandin D2, deoxyprostaglandin E2, deoxyprostaglandin A2, 15-keto-prostaglandin F2α, 15-keto-prostaglandin E2, and epoxyprostaglandin E2.

8. The compound according to claim 1, wherein $R_3$ is an isoprostane selected from the group consisting of isoprostaglandin E2, isoprostaglandin A2, isoprostaglandin F2α, isoprostaglandin B2, isoprostaglandin C2, isoprostaglandin D2, isoprostaglandin J2, deoxyisoprostaglandin D2, deoxyisoprostaglandin E2, deoxyisoprostaglandin A2, deoxyisoprostaglandin J2, 15-keto-isoprostaglandin F2 α, 15-keto-isoprostaglandin E2 and epoxyisoprostaglandin E2.

9. The compound according to claim 1, wherein $R_3$ is a lipoxin selected from the group consisting of lipoxin A4, lipoxin B4 and 15(R)-lipoxin A4.

10. The compound according to claim 1, wherein $R_3$ is a maresin selected from the group consisting of maresin 1 and maresin 2.

11. The compound according to claim 1, wherein $R_3$ is a resolvin selected from the group consisting of resolvin E1, resolvin T1, resolvin D1 and resolvin D2.

12. The compound according to claim 1, wherein $R_3$ is a protectin selected from the group consisting of protectin PDX and protectin D1.

13. The compound according to claim 1, wherein $R_3$ is a prostacyclin selected from the group consisting of 5-{(E)-(1S,5S,6R,7R)-7-hydroxy-6[(E)-(3S,4RS)-3-hydroxy-4-methyl-1-octen-6-inyl]-bicyclo[3.3.0]octan-3-ylidene}pentanyl (iloprost), 5-cis-iloprost, 5-cis-15(R)-iloprost, 15(R)-iloprost, 15-keto-iloprost, carbaprostacyclin, 5-cis-carbaprostacyclin, 13,14-dehydro-15-cyclohexyl, carbaprostacyclin, 5Z-[3aR,3-difluorohexahydro-5R-hydroxy-4R-[3R-hydroxy-4S-methyl-1E-nonen-6aS-ynyl]-2H-cyclopenta[b]furan-2-ylidene]-pentanoyl (16(R)-AFP07), 5Z-[(3aR,4R,5R,6aS)-3,3-difluorohexahydro-5-hydroxy-4-[(1E,3S,4S)-3-hydroxy-4-methyl-1-nonen-6-ynyl]-2H-cyclopenta[b]furan-2-ylidene]-pentanoyl (AFP07), treprostinil, cicaprost, beraprost, ciprostene and 15(R)-prostaglandin $I_2$.

14. The compound according to claim 1, wherein $R_3$ is a compound selected from the group consisting of 10-hydroxydecanyl, 12-hydroxydodecanyl, 15-hydroxyeicosatetraenyl, 12-hydroxy eicosatetraenyl, 8-hydroxyeicosatetraenyl, 9-hydroxyeicosatetrenyl, D,L-threo-9,10,16-trixydroxyhexadecanyl (aleuritic acid residue), (R)-12-hydroxy-cis-9-octadecanyl (12-hydroxyoleic acid residue or ricinoleic acid).

15. The compound according to claim 1, wherein X, Y and Z are O.

16. The compound according to claim 1, wherein the compound is selected from the group consisting of

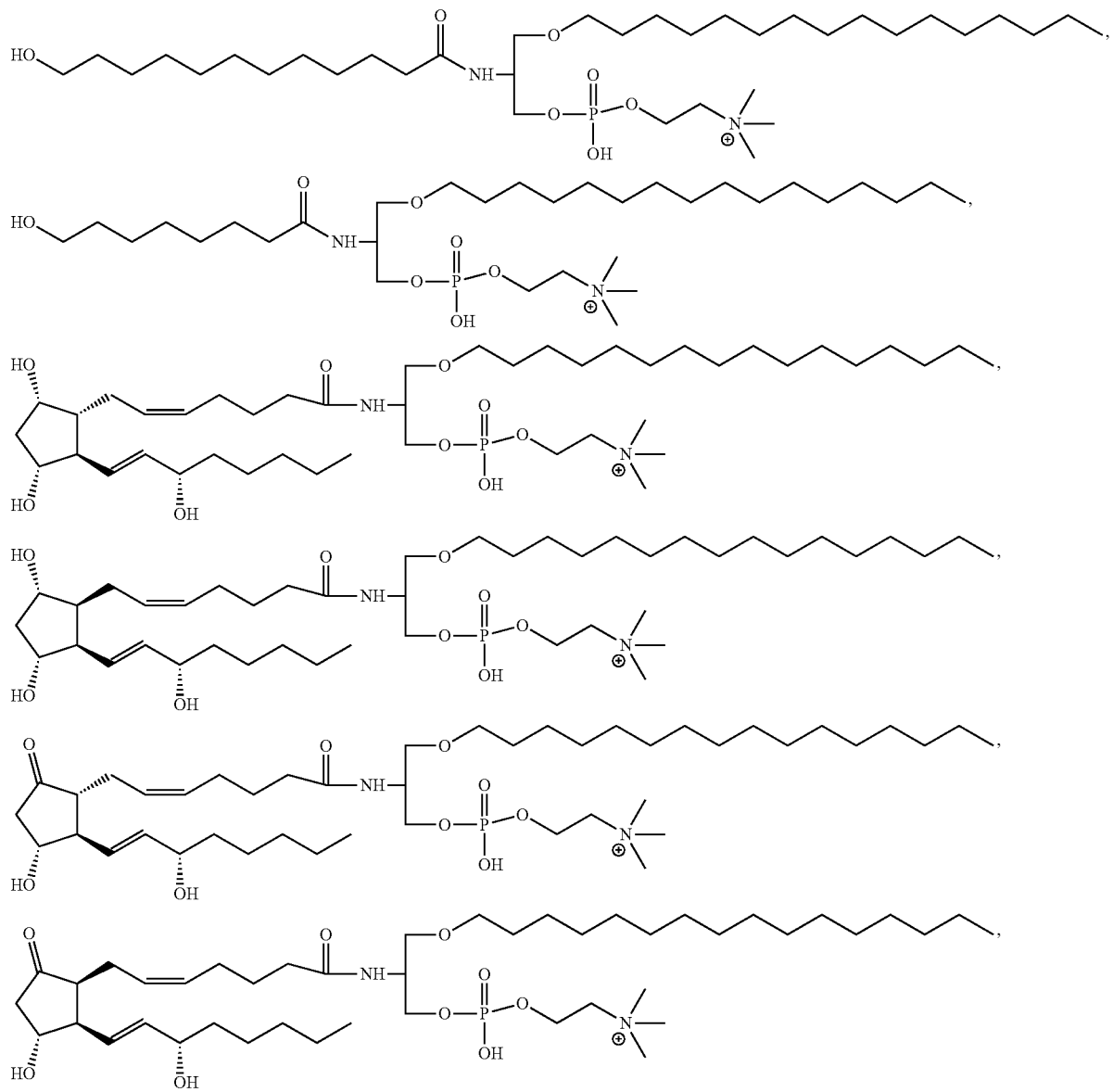

-continued
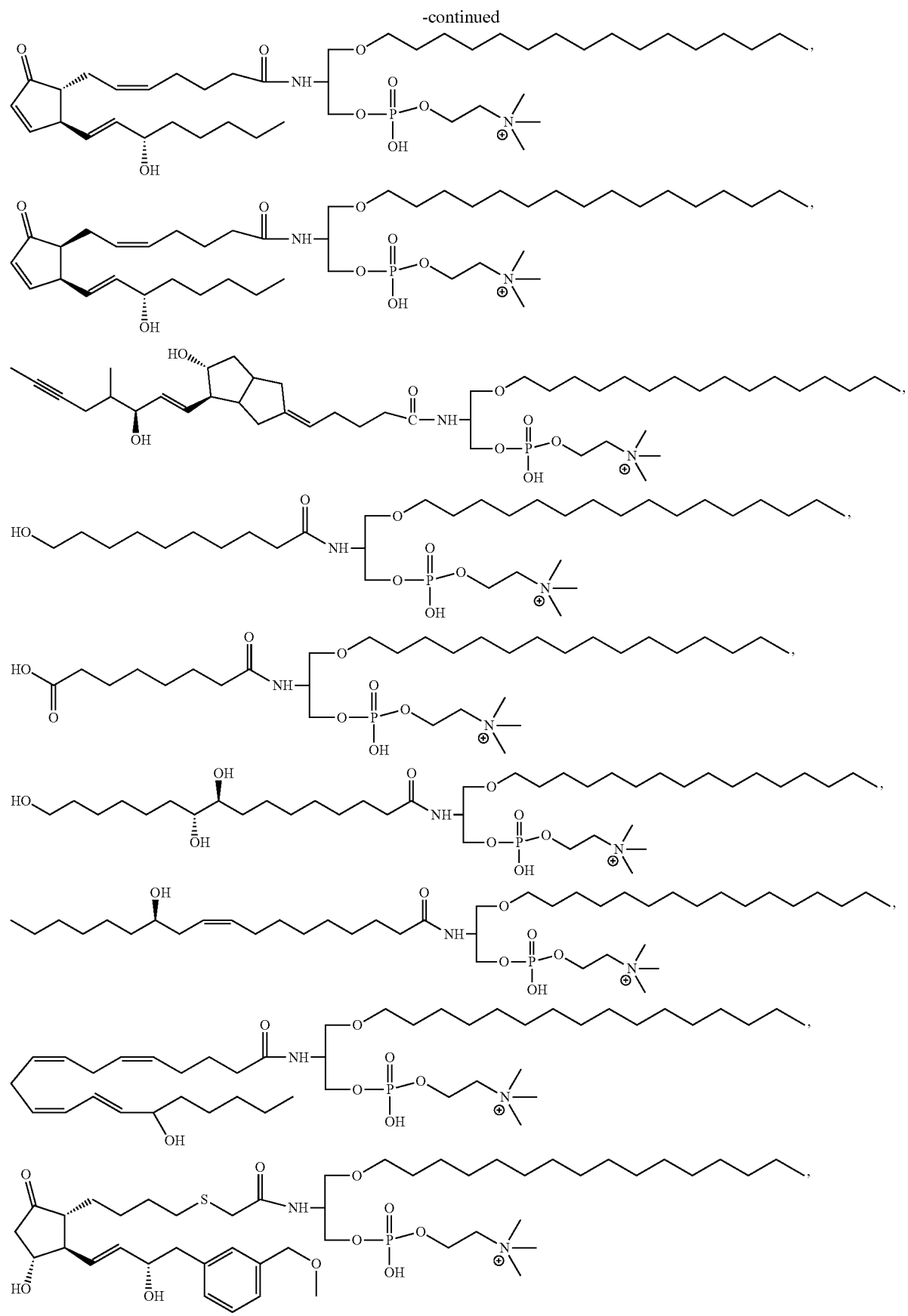

-continued

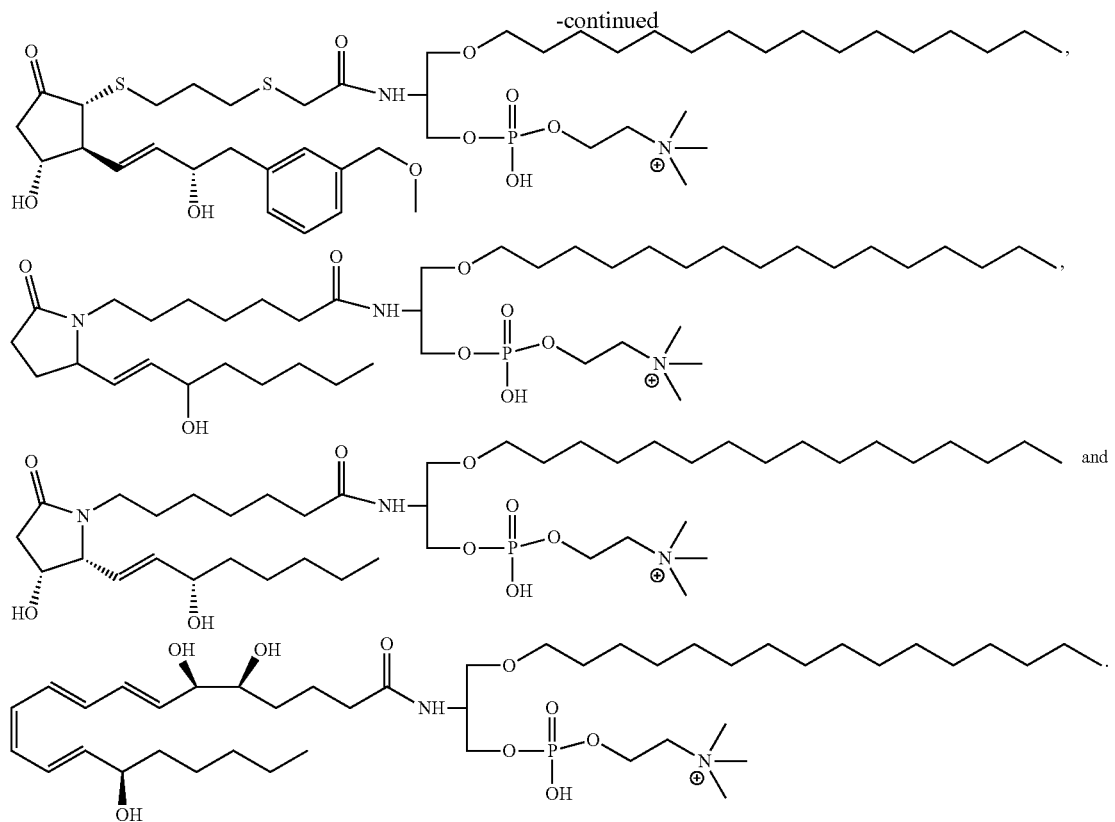

17. A pharmaceutical composition comprising a compound according to claim 1.

18. A method for treating an inflammatory disease or disorder or a disease or disorder associated with Toll-like receptor 2 (TLR2) and/or Toll-like receptor 4 (TLR4) and/or NFkB inflammatory cascade comprising the administration of a compound according to claim 1 to a mammal in need thereof.

19. The method according to claim 18, wherein the mammal is a human.

20. The method according to claim 18, wherein the inflammatory disease or disorder associated with Toll-like receptor 2 (TLR2) and/or Toll-like receptor 4 (TLR4) is Gram-negative sepsis, Gram-positive sepsis, or mixed-type sepsis.

* * * * *